US012767936B2

(12) United States Patent
Lee et al.

(10) Patent No.: US 12,767,936 B2

(45) Date of Patent: Oct. 20, 2026

(54) COMPOSITIONS AND METHODS FOR 2,5-FURAN DICARBOXYLIC ACID PRODUCTION

(71) Applicant: Solugen, Inc., Houston, TX (US)

(72) Inventors: Toni M. Lee, Missouri City, TX (US); Shuai Qian, Houston, TX (US); Brian F. Fisher, Houston, TX (US); Phillip Wiemann, Houston, TX (US); Hans-Joerg Woelk, Hamburg (DE); Gaurab Chakrabarti, Houston, TX (US); Sean Hunt, Houston, TX (US); Konrad V. Miller, Sugar Land, TX (US)

(73) Assignee: SOLUGEN, INC., Houston, TX (US)

( * ) Notice: Subject to any disclaimer, the term of this patent is extended or adjusted under 35 U.S.C. 154(b) by 781 days.

(21) Appl. No.: 17/910,849

(22) PCT Filed: Feb. 25, 2021

(86) PCT No.: PCT/US2021/019690

§ 371 (c)(1),
(2) Date: Sep. 12, 2022

(87) PCT Pub. No.: WO2021/183298

PCT Pub. Date: Sep. 16, 2021

(65) Prior Publication Data

US 2023/0096662 A1 Mar. 30, 2023

Related U.S. Application Data

(60) Provisional application No. 62/988,841, filed on Mar. 12, 2020.

(51) Int. Cl.
*C12N 9/04* (2006.01)
*C12N 9/08* (2006.01)
*C12P 17/04* (2006.01)

(52) U.S. Cl.
CPC ......... *C12N 9/0006* (2013.01); *C12N 9/0065* (2013.01); *C12P 17/04* (2013.01); *C12Y 101/03009* (2013.01); *C12Y 111/01006* (2013.01)

(58) Field of Classification Search
CPC ...... C12N 9/0006; C12N 9/0065; C12P 17/04
See application file for complete search history.

(56) References Cited

U.S. PATENT DOCUMENTS

| | | | |
|---|---|---|---|
| 6,291,648 B1 | 9/2001 | Kawamura et al. | |
| 8,865,921 B2 | 10/2014 | Munoz De Diego et al. | |
| 9,506,090 B2 | 11/2016 | Kambourakis et al. | |
| 2001/0051369 A1 | 12/2001 | Delagrave et al. | |
| 2012/0271060 A1 | 10/2012 | Munoz de Diego et al. | |
| 2014/0106414 A1 | 4/2014 | Kambourakis et al. | |
| 2014/0171683 A1 | 6/2014 | Sieber et al. | |
| 2015/0152452 A1 | 6/2015 | Kalum et al. | |
| 2017/0197930 A1 | 7/2017 | Sokolovskii et al. | |
| 2018/0057897 A1 | 3/2018 | Binder | |
| 2018/0187224 A1* | 7/2018 | Law ............... | C12Y 101/03009 |

FOREIGN PATENT DOCUMENTS

| | | |
|---|---|---|
| CN | 107954959 | 4/2018 |
| JP | 2013-507359 A | 3/2013 |
| JP | 2015-536641 A | 12/2015 |
| WO | 2003/072742 A2 | 9/2003 |
| WO | 2016/141148 A2 | 9/2016 |
| WO | 2016/202858 A1 | 12/2016 |
| WO | 2019/185646 A2 | 10/2019 |

OTHER PUBLICATIONS

Zeng. Efficient One-Pot Synthesis of 2,5-Furandicarboxylic Acid from Sugars over Polyoxometalate/Metal-Organic Framework Catalysts. ChemSusChem. Nov. 8, 2023;16(21):e202300836. Epub Aug. 14, 2023.*
Deacon. Enhanced fructose oxidase activity in a galactose oxidase variant. Chembiochem. Jul. 5, 2004;5(7):972-9.*
Japanese Office Action dated Apr. 15, 2025, for Japanese Application No. 2022-554646 (5 p.).
English Translation of Japanese Office Action dated Apr. 15, 2025, for Japanese Application No. 2022-554646 (6 p.).
PCT/US2021/019690 International Search Report and Written Opinion dated Aug. 4, 2021 (18 p.).
European Search Report dated Aug. 5, 2024, for European Application No. 21767182.5 (13 p.).
Savino, Simone et al., "The Vast Repertoire of Carbohydrate Oxidases: An Overview," Biotechnology Advances vol. 51, Nov. 1, 2021, 107634 (17 p.).
Korean Office Action dated Jan. 26, 2026, for Korean Application No. 10 2022 7035425 (6 p.).

(Continued)

*Primary Examiner* — Yong D Pak
(74) *Attorney, Agent, or Firm* — CONLEY ROSE, P.C.

(57) ABSTRACT

A chemoenzymatic process for the preparation of 2,5-furan dicarboxylic acid includes contacting D-glucose with (i) at least two enzymes selected from the group consisting essentially of galactose oxidase, pyranose 2-oxidase, glucarate dehydratase, catalase and a combination thereof to produce an intermediate; and (ii) a heterogeneous metal catalyst to form 2,5-furan dicarboxylic acid.

16 Claims, 5 Drawing Sheets

Specification includes a Sequence Listing.

(56) References Cited

OTHER PUBLICATIONS

English Summary of Korean Office Action dated Jan. 26, 2026, for Korean Application No. 10 2022 7035425 (3 p.).
Singapore Search Report and Written Opinion dated Oct. 1, 2025, for Singapore Application No. 11202253048X (13 p.).
Chinese Office Action dated May 30, 2026, for Chinese Application No. 202180020764.5 (9 p.).
English Translation of Chinese Office Action dated May 30, 2026, for Chinese Application No. 202180020764.5 (14 p.).
Wang, Jinggang et al., "Research Progress on the Synthesis of Bio-Based Aromatic Platform Chemical 2,5- Furandicarboxylic Acid," Chemical Industry and Engineering Progress, 2017, vol. 36, Issue 2, pp. 672-682 (11 p.).

* cited by examiner

COMPOSITIONS AND METHODS FOR 2,5-FURAN DICARBOXYLIC ACID PRODUCTION

CROSS-REFERENCE TO RELATED APPLICATIONS

This application is a 35 U.S.C. § 371 national stage application of PCT/US2021/019690 filed Feb. 25, 2021, and entitled "Compositions and Methods for 2.5 Furan Dicarboxylic Acid Production." which claims benefit of U.S. provisional patent application Ser. No. 62/988,841 filed Mar. 12, 2020, and entitled "Compositions and Methods for 2,5-Furan Dicarboxylic Acid Production from 5-Hydroxymethylfurfural," each of which is hereby incorporated herein by reference in its entirety for all purposes.

REFERENCE TO AN ELECTRONIC SEQUENCE LISTING

The contents of the electronic sequence listing entitled "3416-00308 Sequence Listing ST25" of size 59 KB and created on Mar. 28, 2021, which is filed herewith is incorporated herein by reference in its entirety.

STATEMENT REGARDING FEDERALLY SPONSORED RESEARCH OR DEVELOPMENT

Not applicable.

FIELD

The present disclosure relates to the production of high purity 2,5-furan dicarboxylic acid. More particularly, this disclosure relates to the chemoenzymatic synthesis of high purity 2,5-furan dicarboxylic acid under mild conditions.

BACKGROUND 2,5-furan dicarboxylic acid (FDCA) is regarded by the US Department of Energy as one of the top 12 value-added chemicals derived from biomass. FDCA is used in the production of a wide array of compounds including succinic acid, isodecylfuran-2,5-dicarboxylate, isononyl furan-2,5-dicarboxylate, dipentyl furan-2,5-dicarboxylate, diheptyl furan-2,5-dicarboxylate, and poly(ethylene dodecanedioate-2,5-furandicarboxylate) (PEDF). FDCA is an important ingredient in the preparation of hexanoic acid, macrocyclic ligands, fungicides, corrosion inhibitors, and tiolene films. The compound can also be used as a precursor in the synthesis of monomers like dichloride-, dimethyl-, diethyl-, or bis(hydroxyethyl)-derivatives for the production of polyesters, polyamides, and plasticizers. FDCA has also been used in medicine as an anesthetic, antibiotic, and chelating agent for the removal of kidney stones. FDCA is particularly interesting as it is a precursor in the synthesis of polyethylene furanoate (PEF), an alternative polymer to petroleum-based polyethylene terepthalate (PET) and polybutylene terephthalate (PEB). The PEF polymer consists of furan-2,5-dicarboxylic acid (FDCA) monomers linked with monoethylene glycol (MEG), another renewable chemical. Structural similarities between the PET monomer para-terepthalic acid (PTA) and FDCA allow for PEF polymerization using existing polyester infrastructure. In addition, PEF exhibits enhanced barrier, thermal, and mechanical properties when compared to PET.

FDCA can be produced from renewable sugars such as glucose and fructose. The conventional approaches to generate FDCA currently include two major competing routes: 1) oxidation and dehydration of fructose through an HMF intermediate, and 2) ketone formation at the C2 or C5 position of aldaric acids to promote furan formation.

SUMMARY

Disclosed herein is a chemoenzymatic process for the preparation of 2,5-furan dicarboxylic acid, the process comprising contacting D-glucose with (i) at least two enzymes selected from the group consisting essentially of galactose oxidase, pyranose 2-oxidase, glucarate dehydratase, catalase, and a combination thereof to produce an intermediate; and (ii) contacting the intermediate with a metal catalyst and acid catalyst to form 2,5-furan dicarboxylic acid.

Also disclosed herein is a chemoenzymatic process for the preparation of 2,5-furan dicarboxylic acid, the process comprising enzymatic oxidation of 5-hydroxymethylfurfural using an enzymatic oxidizing composition comprising one or more enzymes selected from the group consisting of Aryl-alcohol oxidase (AAO) chloroperoxidase (CPO), 5-hydroxymethylfurfural oxidase (HMFO), glyoxal oxidase (GLOX), periplasmic aldehyde oxidase (PaoABC), unspecific peroxygenase (UPO), horseradish peroxidase (HRP), galactose oxidase (GAO) with and without the activating enzyme horseradish peroxidase (HRP), lactoperoxidase (LPO), myeloperoxidase (MPO), eosinophil peroxidase (EPO), thyroid peroxidase (TPO), ovoperoxidase, salivary peroxidase, vanadium haloperoxidase, non-mammalian vertebrate peroxidase (POX), peroxidasin (Pxd), bacterial peroxicin (Pxc), invertebrate peroxinectin (Pxt) and short peroxidockerin (PxDo), short peroxidockerin (Pxt), alpha-dioxygenase (aDox), dual oxidase (DuOx), prostaglandin H synthase or cyclooxygenase (PGHS/CyOx), linoleate diol synthase (LDS), functional variants thereof, and any combination thereof to form an intermediate; and oxidizing the intermediate using a metal catalyst to form 2,5-furan dicarboxylic acid.

BRIEF DESCRIPTION OF DRAWINGS

For a detailed description of the aspects of the disclosed processes and systems, reference will now be made to the accompanying drawings in which.

DETAILED DESCRIPTION

Figure 1:
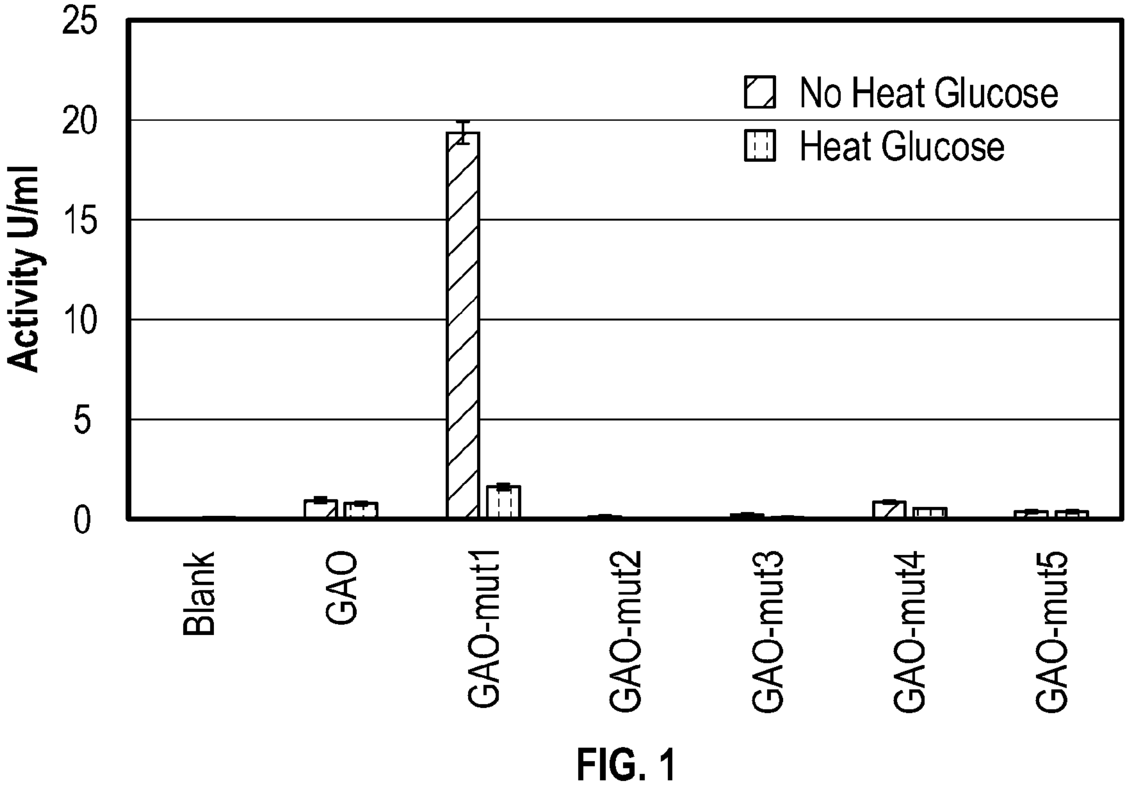
FIG. 1 is a graph of the specific activities for glucose conversion for the samples from Example 1.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied.

Groups of elements of the periodic table are indicated using the numbering scheme indicated in the version of the periodic table of elements published in Chemical and Engineering News, 63(5), 27, 1985. In some instances, a group of elements can be indicated using a common name assigned to the group; for example alkali metals for Group 1 elements, alkaline earth metals for Group 2 elements, transition metals for Group 3-12 elements, and halogens for Group 17 elements, among others.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. The phrase "consisting essentially of" occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials that do not significantly alter the composition or method to which the term is applied. While compositions and methods are described in terms of "comprising" various components or steps, the compositions and methods can also "consist essentially of" or "consist of" the various components or steps.

As previously described, the conventional approaches to generate FDCA currently include two major competing routes: 1) oxidation and dehydration of fructose through an HMF intermediate, and 2) ketone formation at the C2 or C5 position of aldaric acids to promote furan formation. To date, most routes towards FDCA proceed through an HMF intermediate. However, current chemical methods of producing FDCA require harsh reaction conditions (e.g., high temperatures) and are characterized by poor selectivity to the desired product. Accordingly, an ongoing need exists for novel, cost-effective methods of producing FDCA.

Disclosed herein are chemoenzymatic methods for the production of FDCA. In an aspect, a chemoenzymatic method of generating FDCA comprises contacting glucose with a multiple-enzyme system (MES), an acid catalyst, and a metal catalyst to generate the final diacid. In an aspect, the metal catalyst is heterogeneous, alternatively the metal catalyst is homogeneous. One aspect of this method is depicted in Scheme I. Referring to Scheme I, in this process, D-glucose is oxidized using a mutant galactose oxidase (GAO) to form D-glucodialdose. A pyranose-2-oxidase (POX) is used to convert D-glucodialdose to 2-keto-glucodialdose. This molecule is then converted to the diacid over a heterogeneous noble metal catalyst and to the furan form using an acid catalyst. Efficient cyclization may require the diacid instead of the dialdehyde, meaning the heterogeneous catalyst oxidation proceeds before reacting over the acid catalyst. However, if this is not the case and 2-keto-glucodialdose is able to sample the correct furan form at a sufficiently high proportion to promote formation of 2,5-furandicarboxaldehyde (DFF), the acid catalyst step may be conducted before the metal oxidation as is depicted in Scheme II.

SCHEME I

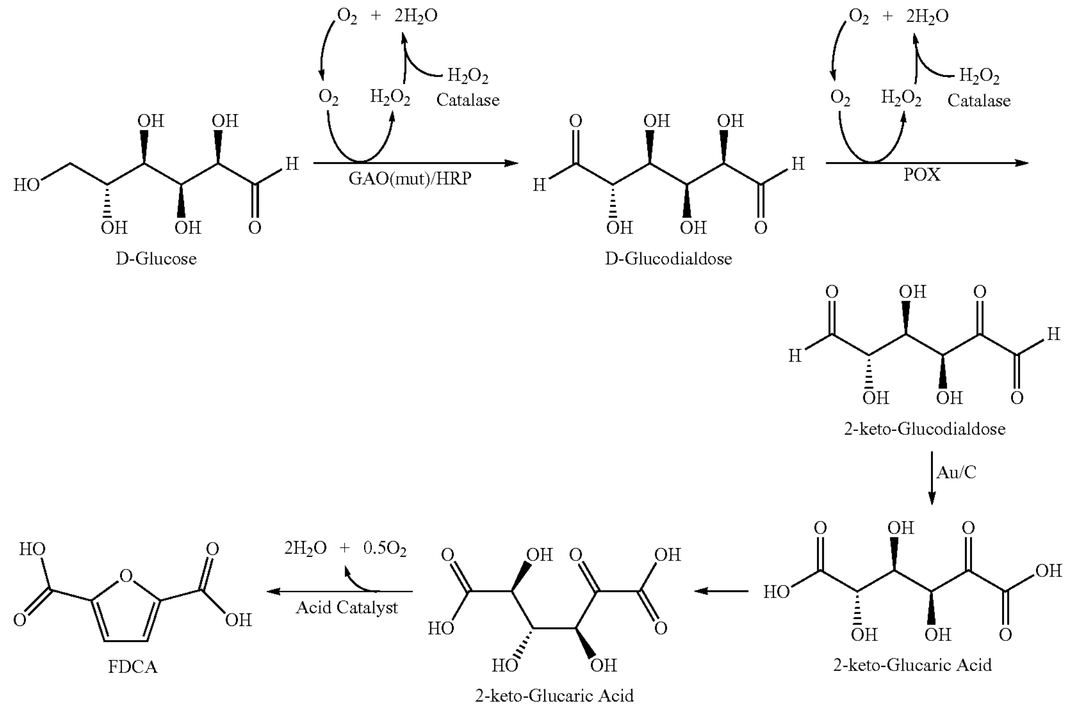

D-Glucose

D-Glucodialdose 2-keto-Glucodialdose

FDCA 2-keto-Glucaric Acid 2-keto-Glucaric Acid

Scheme II

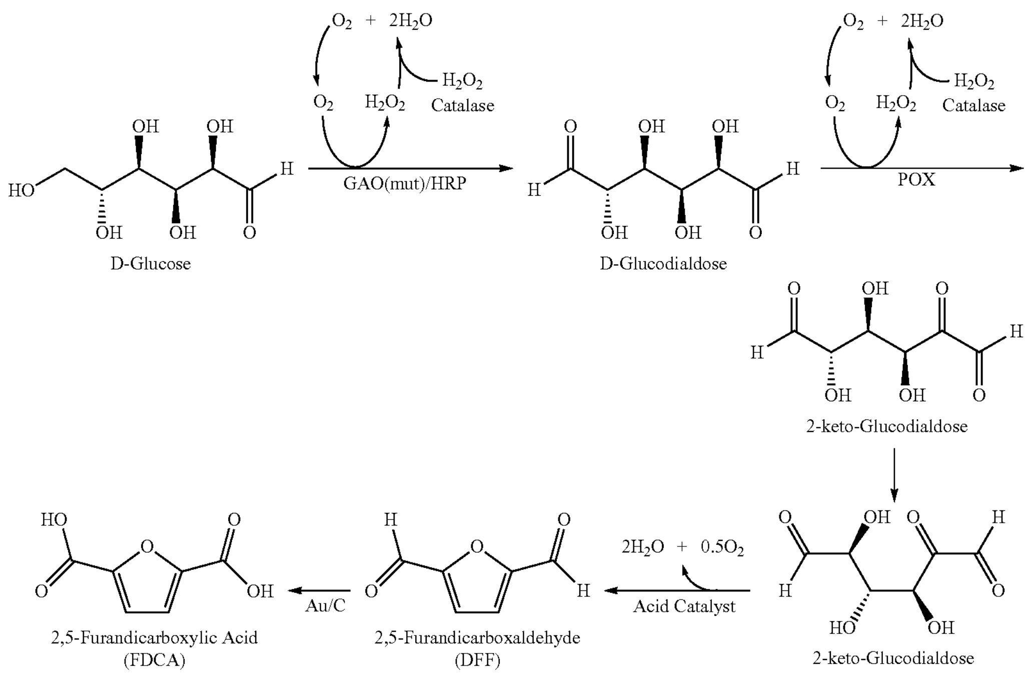

In an alternative aspect for production of FDCA, D-glucose is oxidized using a mutant galactose oxidase (GAO) to form D-glucodialdose. Subsequently, the keto group is formed by an enzyme called glucarate dehydratase (GlucD). This is depicted in Scheme III. This enzyme dehydrates glucodialdose, forming a 5-keto group while removing the 4-hydroxyl as a water. Similar to the reaction cycle depicted in Scheme II, cyclization and oxidation of the terminal aldehydes proceeds over an acid catalyst and heterogeneous noble metal catalyst. The order of the cyclization and terminal oxidation steps may be reversed.

In yet another aspect, D-glucose is oxidized by GAO to form glucodialdose. Glucodialdose may then be oxidized utilizing a metal catalyst to glucaric acid to form 5-keto-4-deoxy-glucodialdose which is subsequently cyclized to form FDCA. This is depicted in Scheme III.

In yet another aspect, D-glucose is oxidized by POX to form 2-ketoglucose, which is then cyclized to form DFF that can then be oxidized as described previously to form FDCA. This is depicted in Scheme IV.

SCHEME III

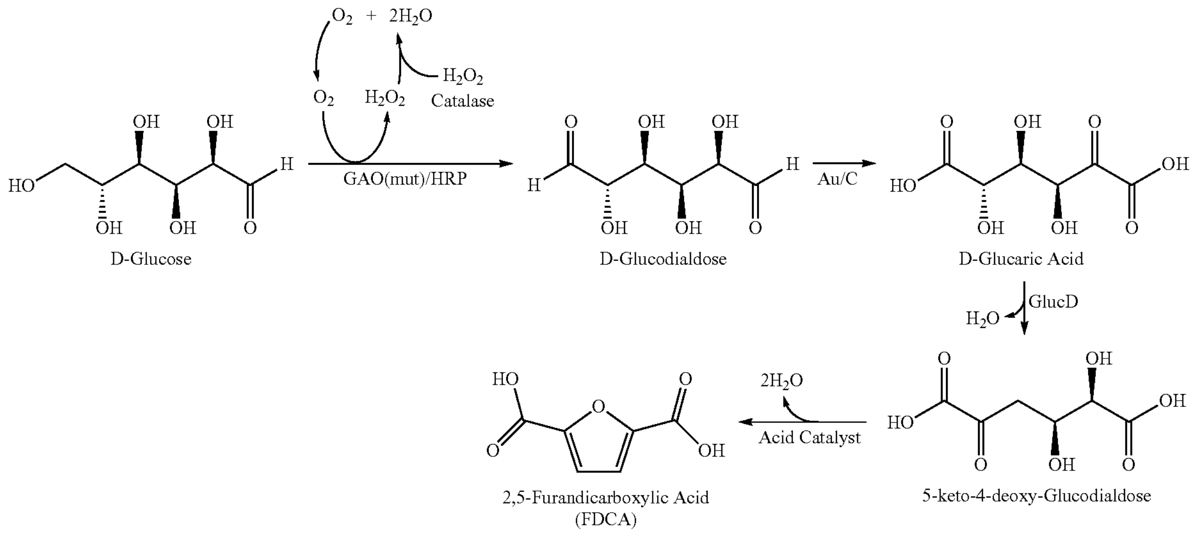

Scheme IV

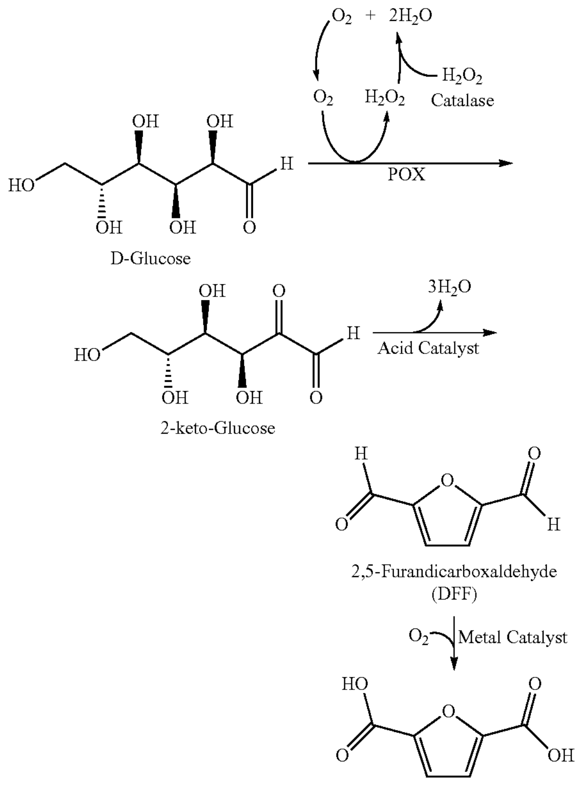

D-Glucose 2-keto-Glucose 2,5-Furandicarboxaldehyde (DFF)

FDCA

The methods of the present disclosure are chemoenzymatic and utilize a combination of enzymes, one or more acid catalysts, and one or more metal catalysts. In an aspect, the enzymes comprise galactose oxidase, pyranose 2-oxidase, glucarate dehydratase, catalase, or a combination thereof. In aspect, the one or more acid catalysts, one or more metal catalysts or both are homogeneous. In an alternative aspect, the one or more acid catalysts, one or more metal catalysts or both are heterogeneous.

In an aspect, the MES comprises a member of the copper radical oxidase family. For example, and without limitation, a copper radical oxidase suitable for use in the present disclosure is galactose oxidase (GAO, EC 1.1. 3.9). GAO is one of the most extensively studied alcohol oxidases with respect to both mechanistic investigations and practical applications. Other members in the copper radical oxidase family may be suitably employed in the present disclosure.

GAO is secreted by some fungal species, particularly *Fusarium graminearum* (also known as *Gibberella zeae*), to aid in the degradation of extracellular carbohydrate food sources through catalyzing the oxidation of primary alcohols to aldehydes while generating hydrogen peroxide. The native function of GAO is the oxidation of D-galactose at the C6 position to generate D-galacto-hexodialdose. A small molecule (potassium ferricyanide) or auxiliary enzyme (i.e., horseradish peroxidase or HRP) is typically included to facilitate GAO activity. Typically, HRP is added to the reaction at a tenth of the weight percent (wt. %) of GAO. Catalase is also added to decompose hydrogen peroxide. Although the GAO is promiscuous, the native form is unable to bind glucose due to steric clashes with F464 and F194 in the active site and the equatorial C4 hydroxyl group on glucose. Efforts to engineer GAO to accept D-glucose as a substrate to form the C6 aldehyde have resulted in improved activity as shown in Table 1. The M-RQW variant (R330K, Q406T, W290F) shows a specific activity of 1.6 U $mg^{-1}$. Another variant, the Des3-2 (Q326E, Y329K, R330K) showed four times higher activity on glucose than the native enzyme. In addition, the mutation C383S was found to improve catalytic efficiency up to three times by reducing the KM of the enzyme on non-native substrates guar gum and methylgalactose through improved binding of the catalytic copper ion. Tables 1 and 2 provide listings of some GAO mutants that may be useful in the methods of the present disclosure.

TABLE 1

| Enzyme Name | Mutations | Benefits |
|---|---|---|
| M-RQW | R330K Q406T W290F | 1.6 U/mg on glucose |
| Des3-2 | Q326E Y329K R330K | 4x activity on glucose vs WT |
| NA | C383S | Reduces $K_M$ through improved copper binding |
| M1 | S10P M70V P136 G195E V494A N535D | Improves *E. coli* expression and solubility |
| N6M1 | A2A (GCC→GCA) S3S (TCA→TCT) I5I (ATC→ATT) | Silent N-term mutations for enhanced *E. coli* expression |
| NA | F194T C383E N245W/R | Improved specific activity of up to 3 U/mg with N245R and C383E in N6M1 background |
| NA | W290F R330K Q406T Y405F Q406E | 1.6 μM/min conversion on glucose |

TABLE 2

| Name | Starting Mut | Additional mutations |
|---|---|---|
| M1 | wild-type | S10P M70V P136P G195E V494A N535D |
| M-RQW | M1 | R330K Q406T W290F I463P |
| GAO | M-RQW | C383S |
| GAO-mut1 | GAO | Y405F Q406E |
| GAO-mut2 | GAO | F194T |
| GAO-mut3 | GAO | C383E |
| GAO-mut4 | GAO | N245R |
| GAO-mut5 | GAO | Q326E Y329K |

In an aspect, a GAO suitable for use in the present disclosure may have any of SEQ ID NO.:1 to SEQ ID NO.:6.

In an aspect, the MES comprises a pyranose 2-oxidase (E.G. 1.1.3.10). Pyranose 2-oxidase (POX) is an flavin-dependent oxidoreductase, and a member of the glucose-methanol-choline (GMC) superfamily of oxidoreductases. POX oxidizes several monosaccharides including D-glucose, D-galactose, and D-xylose, while concurrently oxygen is reduced to hydrogen peroxide. For example, in lignocellulose-degrading fungi POX catalyzes the oxidation of α or β-D-glucose to 2-ketoglucose concomitantly with hydrogen peroxide formation during lignin solubilization.

In fungi, POX is extracellularly associated with membrane-bound vesicles or other membrane structures in the periplasmic space of hyphae. POX homologs are also found in actinobacteria, protobacteria, and bacilli species. POX enzymes from *Spongipellis unicolor* (aka *Polyporus obtusus*), *Phanerochaete chrysosporium* (PDB 4MIF), *Trametes multicolor* (aka *Trametes ochracea* PDB 1TT0), *Peniophora gigantea* (PDB 1TZL), *Aspergillus nidulans, A. oryzae, Irpex lacteus, Arthrobacter siccitolerans*, and *Kitasatospora aureofaciens* (aka *Streptomyces aureofaciens*) have been characterized. Although most POX enzymes exist as homotetramers with FAD covalently bound to a histidine, exceptions exist. POX is a monomer in solution and non-covalently binds FAD. KaPOX forms dimers in solution. In addition to this oxidase activity, POX shows pronounced activity with alternative electron acceptors that include various quinones or (complexed) metal ions. In an aspect, a POX suitable for use in the present disclosure may have any of SEQ ID NO.:7 to SEQ ID NO.:11.

In an aspect, the MES comprises a glucarate dehydratase (E.C. 4.2.1.40). GluD belongs to the mechanistically diverse enolase superfamily, specifically the glucarate dehydratase subgroup. GluD catalyzes the dehydration of both D-glucarate and L-idarate to form 5-keto-4-deoxyglucarate (KDG) as well as the epimerisation of the two substrates. In the first step, the His 339 residue acts as a general base towards the C5 atom of D-glucarate, while Lys 207 acts as a general base towards the related epimer L-Idarate. Each residue is associated with a different stereo selective function; Lys 207 acts as an S specific base, while His 339 acts as an R specific base. The enolate anion intermediate is stabilized by hydrogen bonds to residues Lys 205 and Asn 237, as well as interaction with the catalytically essential divalent Mg cation.

In an aspect, an MES of the present disclosure comprises a catalase (E.C. 1.11.1.61). CAT is a tetrameric, heme-containing, antioxidant enzyme present in all aerobic organisms. Catalase catalyzes the decomposition of $H_2O_2$ into water and oxygen.

In an aspect, any of the enzymes present in the MES is a wild type enzyme, a functional fragment thereof, or a functional variant thereof. As used herein, "fragment" is meant to include any amino acid sequence shorter than the full-length enzyme (e.g., AOX), but where the fragment maintains a catalytic activity sufficient to meet some user or process goal. Fragments may include a single contiguous sequence identical to a portion of the enzyme sequence. Alternatively, the fragment may have or include several different shorter segments where each segment is identical in amino acid sequence to a different portion of the amino acid sequence of the enzyme but linked via amino acids differing in sequence from the enzyme. Herein, a "functional variant" of the enzyme refers to a polypeptide that has at one or more positions of an amino acid insertion, deletion, or substitution, either conservative or non-conservative, and wherein each of these types of changes may occur alone, or in combination with one or more of the others, one or more times in a given sequence but retains catalytic activity.

In the alternative or in combination with the aforementioned mutations, an enzyme in the MES may be mutated to improve the catalytic activity. Mutations may be carried out in order to enhance the protein or a homolog activity, increase the protein stability in the presence of products and/or hydrogen peroxide, and increase protein yield.

Herein, reference is made to "sources" of enzymes. It is to be understood this refers to the biomolecule as expressed by the named organism. It is contemplated the enzyme may be obtained from the organism or a version of said enzyme (wildtype or recombinant) provided as a suitable construct to an appropriate expression system.

In an aspect, any enzyme of the type disclosed herein may be cloned into an appropriate expression vector and used to transform cells of an expression system such as *E. coli, Saccharomyces* sp., *Pichia* sp., *Aspergillus* sp., *Trichoderma* sp., or *Myceliophthora* sp. A "vector" is a replicon, such as plasmid, phage, viral construct, or cosmid, to which another DNA segment may be attached. Vectors are used to transduce and express a DNA segment in cells. As used herein, the terms "vector" and "construct" may include replicons such as plasmids, phage, viral constructs, cosmids, Bacterial Artificial Chromosomes (BACs), Yeast Artificial Chromosomes (YACs) Human Artificial Chromosomes (HACs), and the like into which one or more gene expression cassettes may be or are ligated. Herein, a cell has been "transformed" by an exogenous or heterologous nucleic acid or vector when such nucleic acid has been introduced inside the cell, for example, as a complex with transfection reagents or packaged in viral particles. The transforming DNA may or may not be integrated (covalently linked) into the genome of the cell.

In an aspect, the gene of an enzyme disclosed herein is provided as a recombinant sequence in a vector where the sequence is operatively linked to one or more control or regulatory sequences. "Operatively linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and refer to polynucleotide sequences, which are necessary to affect the expression of coding sequences to which they are operatively linked. Expression control sequences are sequences that control the transcription, post-transcriptional events, and translation of nucleic acid sequences. Expression control sequences include appropriate transcription initiation, termination, promoter, and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

In an aspect, the enzymes suitable for use in an MES of the type disclosed herein may further include one or more purified cofactors. Herein, a "cofactor" refers to non-protein chemical compound that modulates the biological activity of the enzyme. Many enzymes require cofactors to function properly. Nonlimiting examples of purified enzyme cofactors suitable for use in the present disclosure include thiamine pyrophosphate, NAD+, NADP+, pyridoxal phosphate, methyl cobalamin, cobalamine, biotin, Coenzyme A, tetrahydrofolic acid, menaquinone, ascorbic acid, flavin mononucleotide, flavin adenine dinucleotide, and Coenzyme F420. Such cofactors may be included in the MES and/or be added at various points during a reaction. In some aspects, cofactors included with the MES may be readily regenerated with oxygen and/or may remain stable throughout the lifetime of the enzyme(s).

In one or more aspects, any enzyme component of the MES is present in an amount in the MES and/or reaction mixture sufficient to provide some user and/or process desired catalytic activity. In such aspects, any of the enzymes disclosed herein may be present in an amount ranging from about 0.0001 wt. % to about 1 wt. %, alternatively from about 0.0005 wt. % to about 0.1 wt. % or alternatively from about 0.001 wt. % to about 0.01 wt. % based on the total weight of the MES.

In the reactions depicted in Schemes 1 through V, the MES acts to initially oxidize glucose which is subsequently reacted to form an intermediate that is dehydrated. For example, methods of the present disclosure involve dehydration of the intermediates 5-keto-4-deoxy-glucarate, 5-keto-4-deoxy-glucodialdose, 2-keto-glucodialdose, 2-keto-glucaric acid, and/or 2-keto-glucose to form DFF. In an aspect, dehydration is carried out in the presence of an acid catalyst.

In an aspect, the acid catalyst that is employed to facilitate dehydration of the aforementioned intermediates is a Bronsted acid or contains strong Bronstead acid sites that are characterized by ability to provide a proton or hydronium ion in the reaction mixture. Bronstead acids suitable for use in the present disclosure include homogeneous acidic catalysts or heterogeneous acidic catalysts tested for furan formation in glucaric acid. In an aspect, the acid catalyst comprises ion exchange resins (such as DIAION series, Amberlyst-15), sulfonated silica, zeolites, niobium oxide, mineral acids such as HCl, or a combination thereof. In an aspect, the acid catalyst may be present in an amount effective to catalyze conversion of the intermediate. In an aspect, the acid catalyst is present in a suitable solvent such as dimethyl formamide or dimethyl sulfoxide. For example, the acid catalyst may be present in an amount of from about 0.1 wt. % about 0.2 wt. % based on the total weight of the reaction mixture, alternatively from about 0.001 wt. % to about 2.0 wt. % or alternatively from about 0.001 wt. % to about 20 wt. %.

In one or more aspects of the present disclosure, a final oxidation step is carried out to convert an aldehyde into a carboxylic acid, such as depicted in Schemes I through IV. In an aspect of the present disclosure, the oxidation can be carried out using a metal catalyst, alternatively a supported metal catalyst. In an aspect, the metal catalyst comprises a supported metal catalyst such as a heterogeneous metal catalyst or a homogenous metal catalyst (HMC). In an aspect, the support comprises carbon, silica, alumina, titania ($TiO_2$), zirconia ($ZrO_2$), a zeolite, or any combination thereof, which contains less than about 1.0 weight percent (wt. %), alternatively less than about 0.1 wt. % or alternatively less than about 0.01 wt. % $SiO_2$ binders based on the total weight of the support.

Suitable support materials are predominantly mesoporous or macroporous, and substantially free from micropores. For example, the support may comprise less than about 20% micropores. In an aspect, the support of the HMC is a porous nanoparticle support. As used herein, the term "micropore" refers to pores with a diameter of <2 nm, as measured by nitrogen adsorption and mercury porosimetry methods and as defined by IUPAC. As used herein, the term "mesopore" refers to pores with a diameter of from ca. 2 nm to ca. 50 nm, as measured by nitrogen adsorption and mercury porosimetry methods and as defined by IUPAC. As used herein, the term "macropore" refers to pores with diameters larger than 50 nm, as measured by nitrogen adsorption and mercury porosimetry methods and as defined by IUPAC.

In an aspect, the HMC support comprises a mesoporous carbon extrudate having a mean pore diameter ranging from about 10 nm to about 100 nm, and a surface area greater than about 20 $m^2$ $g^{-1}$ but less than about 300 $m^2$ $g^{-1}$. Supports suitable for use in the present disclosure may have any suitable shape. For example, the support may be shaped into 0.8-3.0 mm trilobes, quadralobes, or pellet extrudates. Such shaped supports enable the used of fixed trickle bed reactors to perform the final oxidation step under continuous flow.

In an aspect, the HMC comprises metals of main group IV, V, VI, alternatively the metal is from subgroup I, IV, V, VII, alternatively the HMC comprises gold, Au. In one or more aspects, the metal comprises a Group 8 metal (e.g., Re, Os, Ir, Pt, Ru, Rh, Pd, Ag), a 3d transition metal, an early transition metal, or a combination thereof. In an alternative aspect, a dehydration catalyst comprises hafnium, tantalum, zinc, or a combination thereof on a support such as a zeolite or a β-zeolite. In an aspect, a metal catalyst suitable for use in the present disclosure comprises a metal oxide, zirconia doped with alkaline-earth elements, rare earth orthophosphate catalyst, ruthenium, or a combination thereof.

The HMC may be prepared using any suitable methodology. For example, the HMC may be prepared using gas phase reduction of the support (e.g., carbon) impregnated with metal salts in hydrogen at temperatures ranging from greater than about 200° C. to about 600° C. In an alternative aspect, the HMC may be prepared using liquid phase reduction of the support impregnated with metal salts immersed in an aqueous oxygenate (e.g., formate, gluconate, citrate, ethylene glycol, etc.) solution at temperature between about 0° C. and about 100° C. Alternatively, the impregnated support can be loaded into the hydrogenation reactor in a non-reduced form and reduced on stream by the reactants of the process during startup. Liquid Phase Reduction (LPR) is a synthetic method to obtain a core-shell dispersion of the active metallurgy over a surface annulus of the extrudate.

In an aspect, materials of the type disclosed herein are prepared via incipient wetness or bulk adsorption of a metal precursor salt solution onto the extrudate support followed by either Gas Phase Reduction (GPR) at temperatures between 100° C. and 500° C. under an $H_2/N_2$ atmosphere or followed by Liquid Phase Reduction (LPR) using an alkaline aqueous solution.

In one or more alternative aspects, a method of the present disclosure comprises enzymatic oxidation of HMF, under mild reaction conditions, to produce an intermediate. In an aspect, a method of the present disclosure further comprises oxidation of the intermediate by a metal catalyst, alternatively a heterogeneous metal catalyst (HMC) to produce the FDCA. This scheme is generally depicted in Scheme V.

Scheme V

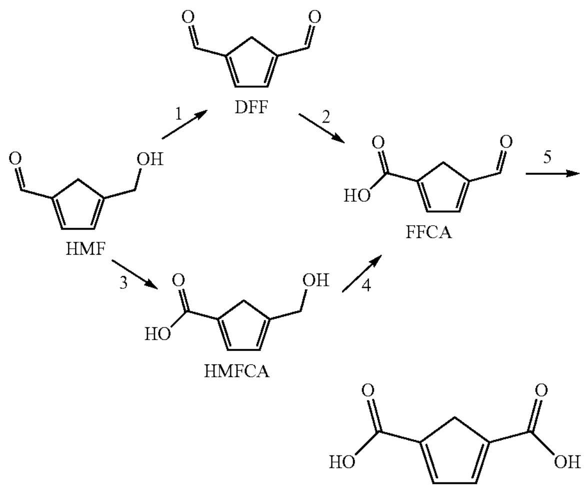

DFF

HMF

FFCA

HMFCA

FDCA

Without wishing to be limited by theory, oxidases, which typically generate one molecule of hydrogen peroxide for each oxidation performed, can be combined with peroxygenases or peroxidases which use hydrogen peroxide as an oxidant to catalyze another oxidation. This not only removes highly reactive hydrogen peroxide from the solution, but also provides peroxide which is necessary for peroxygenase/peroxidase function.

In an aspect, a method of producing FDCA comprises enzymatic oxidation of HMF by an enzymatic oxidizing composition (EOC). In an aspect, the EOC comprises one or more enzymes selected from the group consisting of Aryl-alcohol oxidase (AAO), chloroperoxidase (CPO), 5-hydroxymethylfurfural oxidase (HMFO), glyoxal oxidase (GLOX), periplasmic aldehyde oxidase (PaoABC), unspecific peroxygenase (UPO), horseradish peroxidase (HRP), galactose oxidase (GAO) with and without the activating enzyme horseradish peroxidase (HRP), lactoperoxidase (LPO), myeloperoxidase (MPO), eosinophil peroxidase (EPO), thyroid peroxidase (TPO), ovoperoxidase, salivary peroxidase, vanadium haloperoxidase, non-mammalian vertebrate peroxidase (POX), peroxidasin (Pxd), bacterial peroxicin (Pxc), invertebrate peroxinectin (Pxt) and short peroxidockerin (PxDo), short peroxidockerin (Pxt), alpha-dioxygenase (aDox), dual oxidase (DuOx), prostaglandin H synthase, cyclooxygenase (PGHS/CyOx), linoleate diol synthase (LDS), functional variants thereof and any combination thereof. Enzymes of the type disclosed herein may be isolated from any suitable source. Nonlimiting examples of enzymes suitable for use in the present disclosure along with their catalytic efficiencies ($k_{cat}$) are presented in Table 3 which also provides the step of Scheme 1 that may be catalyzed by the enzyme.

TABLE 3

| Step | Enzyme | $k_{cat}$ ($S^{-1}$) |
|---|---|---|
| 1 | GAO (Novozymes) | 0.7 |
| 1 | *Pleurotus ostreatus* AAO | 2.95 |
| 1 | *Pleurotus eryngii* AAO | 0.34, 3.65 |

TABLE 3-continued

| Step | Enzyme | $k_{cat}$ ($S^{-1}$) |
|---|---|---|
| 1 | *Pleurotus eryngii* AAO Bantha (F501W) | 18.8 |
| 1 | *Agrocybe aegerita* UPO | 222.2 (split with step 3) |
| 1 | *Methylovorus* sp. strain MP688 HMFO | 9.9 |
| 1 | *Methylovorus* sp. strain MP688 7xHMFO | 11.8 |
| 1 | *Pycnoporus cinnabarinus* GLOX1 | 1.59 |
| 1 | *Pycnoporus cinnabarinus* GLOX2 | 0.56 |
| 1 | *Pycnoporus cinnabarinus* GLOX3 | 0.75 |
| 2 | *Pleurotus eryngii* AAO | 0.86 |
| 2 | *Pleurotus eryngii* AAO Bantha (F501W) | ND |
| 2 | *Agrocybe aegerita* UPO | 29.2 |
| 2 | *Methylovorus* sp. strain MP688 HMFO | 1.6 |
| 2 | *Pycnoporus cinnabarinus* GLOX1 | 4.38 |
| 2 | *Pycnoporus cinnabarinus* GLOX2 | 0.21 |
| 2 | *Pycnoporus cinnabarinus* GLOX3 | 0.18 |
| 3 | *Agrocybe aegerita* UPO | 222.2 (split with step 1) |
| 4 | *Methylovorus* sp. strain MP688 HMFO | 8.5 |
| 4 | $GAOM_{3-5}$ and HRP | ND |
| 5 | *Aspergillus* catalase | ND |
| 5 | *Methylovorus* sp. strain MP688 HMFO | ND |
| 5 | *Agrocybe aegerita* UPO | ND |
| 5 | *Pleurotus eryngii* AAO Bantha (F501W) | ND |
| 5 | *Pycnoporus cinnabarinus* GLOX1 | 0.03 |
| 5 | *Pycnoporus cinnabarinus* GLOX2 | 2.02 |
| 5 | *Pycnoporus cinnabarinus* GLOX3 | 0.04 |

Herein, the $k_{cat}$ refers to the turnover rate, turnover frequency, or turnover number. This constant represents the number of substrate molecules that can be converted to product by a single enzyme molecule per unit time (usually per minute or per second).

As will be understood by one of ordinary skill in the art with the benefit of the present disclosure, reactions of the type disclosed herein (e.g., AAO oxidation of HMF) may result in the production of byproducts that can detrimentally impact other components of the reaction mixture. For example, hydrogen peroxide may degrade the enzymes of the EOG resulting in a reduced catalytic efficiency. In such aspects, the detrimental effects of hydrogen peroxide may be mitigated such as by introduction of a catalase (E.G. 1.11.1.61), which not only degrades the hydrogen peroxide but will also generate oxygen to drive oxidase function.

In an aspect, an EOC of the present disclosure comprises (i) an oxidase; (ii) a peroxidase; and (iii) a catalase. Alternatively, an EOC of the present disclosure comprises (i) an oxidase; (ii) a peroxygenase and (iii) a catalase; alternatively (i) an oxidase and (ii) a peroxidase; alternatively (i) an oxidase and (ii) a peroxygenase; alternatively an oxidase or alternatively a peroxidase. Each of these enzymes may be of the type disclosed herein.

In an aspect, one or more enzymes of an EOC of the present disclosure is characterized by a $k_{cat}$ of equal to or greater than about 9 $s^{-1}$, alternatively equal to or greater than about 50 $s^{-1}$, or alternatively equal to or greater than about 100 $s^{-1}$.

In an aspect, an EOC of the type disclosed herein may be utilized to produce an intermediate in the conversion of HMF to FDCA. Nonlimiting examples of intermediates that may be produced using an EOC of the type disclosed herein include diformyl furan (DFF), 5-hydroxymethyl-2-furoic acid (HMFCA), and 5-formyl-2-furancarboxylic acid (FFCA). In an aspect, an EOC of the present disclosure when reacted with HMF forms one or more intermediates selected from the group consisting of diformyl furan (DFF), 5-hydroxymethyl-2-furoic acid (HMFCA), and 5-formyl-2-furancarboxylic acid (FFCA). An intermediate produced by reacting an EOC with HMF (e.g., diformyl furan) may be further oxidized to produce FDCA using a transition metal catalyst.

Figure 7:
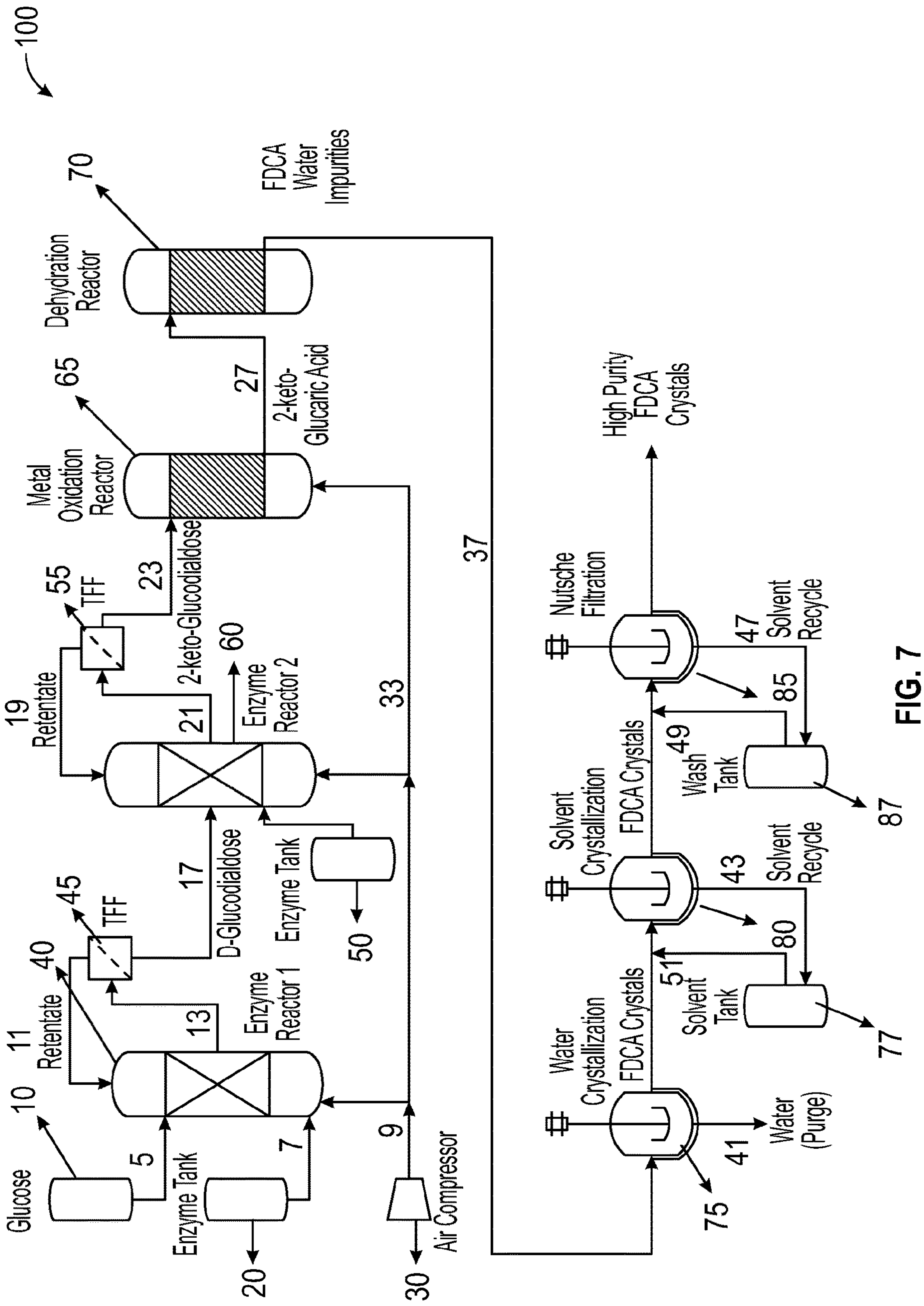
FIG. 7 is an aspect of a process flow diagram or a chemoenzymatic process of the type disclosed herein.

In an aspect, chemoenzymatic processes of the type disclosed herein may be carried out in any suitable reactor. An aspect of a suitable reactor is depicted in FIG. 7. Referring to FIG. 7, a first enzymatic reactor 40 could be a sparged bubble column, an air lift column, a stirred sparged bioreactor, or a falling film high pressure oxidation vessel. The reactants, glucose, and a MES, can be introduced to the reactor from storage containers 10 and 20 via conduits 5 and 7 respectively. In an aspect, the enzyme reactor 40 may operate at temperatures of less than about 100° C., alternatively at temperatures ranging from about 20° C. to about 60° C. and at pressures ranging from about 1 bar to about 15 bar. In an aspect, in the enzyme reactor 40 glucose is converted enzymatically by GAO and HRP to D-glucodialdose, with catalase present to degrade hydrogen peroxide for enzyme stability. Further, the enzyme reactor 40 may be sparged with both compressed air (for molecular oxygen) which may be supplied by an air compressor 30 via conduit 9. While not shown, pH can be controlled by the addition of strong acids, bases, or buffers. Effluent from the enzyme reactor 40 may be sent via conduit 13 to a tangential flow filter (TFF) 45 in order to preserve enzymes in the enzyme reactor and recycled as retentate via conduit 11, with D-glucodialdose permeate flowing further down the process to the second enzymatic reactor 60 via conduit 17.

The second enzymatic reactor 60 could be a sparged bubble column, an air lift column, a stirred sparged bioreactor, or a falling film high pressure oxidation vessel. In an aspect, the second enzyme reactor 60 may operate at temperatures of less than about 100° C., alternatively at temperatures ranging from about 20° C. to about 60° C. and at pressures ranging from about 1 bar to about 15 bar. In the second enzyme reactor 60, D-glucodialdose is converted enzymatically by POX to 2-keto-glucodialdose, with catalase present to degrade hydrogen peroxide for enzyme stability. In the alternative as depicted in Scheme III GlucD replaces POX. The second enzyme reactor 60 may be sparged with compressed air (for molecular oxygen). While not shown, pH can be controlled by the addition of strong acids, bases, or buffers. Effluent from the second enzyme reactor 60 may be sent to a TFF 55 via conduit 21 to preserve enzymes in the enzyme reactor as recycled retentate via conduit 19, with 2-keto-glucodialdose permeate flowing further down the process via conduit 23 to the metal oxidation reactor 65 and dehydration reactor 70.

In an aspect, permeate from the second enzyme reactor 60 is fed downstream to the metal oxidation reactor 65, where 2-keto-glucodialdose is converted to 2-keto-glucaric acid. In one or more aspects, the oxidation reactor 65 is operated as a trickle-bed reactor, utilizing metal catalysts of the type disclosed herein. The oxidation reactor 65 may be fed 2-ketoglucodialdose from the top and fed with high pressure air (to provide molecular oxygen) from the bottom, to ensure proper bed wetting and mass transfer. The oxidation reactor 65 may be operated at pressures ranging from about 100° C. to about 200° C. and pressures ranging from about 10 to about 100 bar. In an aspect, the reactor product is removed from the bottom and passed on to the dehydration reactor 70.

2-keto-glucaric acid leaving the metal oxidation reactor 65 may be converted to FDCA via dehydration in the dehydration reactor 70. In an aspect, the dehydration reactor 70 is operated in either upstream or downstream configuration. The dehydration reactor 70 may be charged with an immobilized strong acid exchange catalyst, as described previously herein. The dehydration reactor 70 may operate at temperatures ranging from about 160° C. to about 200°. For example, the dehydration reaction may take place with liquid water at elevated pressures.

In an aspect, the dehydration reactor product includes a mixture of water and FDCA, along with side product impurities. The dehydration reactor product stream may be transferred via conduit 37 to a purification train consisting of a water crystallization unit 75, a solvent crystallization unit 80, and a Nustche Filter 85. As FDCA solubility in water is a strong function of temperature, the water crystallization unit 75 may be a cooling crystallizer or a cooling and vacuum crystallizer. In an aspect, FDCA crystals are then separated via filtration and sent to a second, organic solvent crystallizer.

In the organic solvent crystallizer 80, the solvent may be 1-butanol, isobutanol, methanol, or another suitable organic solvent. Without wishing to be limited by theory, by switching between water and an organic solvent, different impurities can be removed in the mother liquor. FDCA is then crystallized out either by cooling or vacuum crystallization, with crystals removed and passed to a Nutsche filter 85. Organic solvent can be removed and regenerated via distillation to remove non-volatile impurities.

FDCA crystals are then washed in a Nutsche Filter 85 to remove any residual impurities. A polar, aprotic solvent like acetonitrile may be utilized, as (1) this would solvate impurities not previously picked up in water, a polar protic solvent, or 1-butanol, a non-polar protic solvent, and (2) FDCA is only sparingly soluble in acetonitrile. Acetonitrile leaving the Nutsche filter 85 could then be regenerated via distillation to remove non-volatile impurities. Highly pure FDCA crystals are then removed from the Nutsche Filter 85 as the final product.

Although the above drawing is at PFD level of detail, not all process interconnections are shown such as spillbacks, block and bleeds, recycle lines, control valves, cooling/heating elements, pumps, intermediate tankage, antifoam, etc.

In an aspect, the methods disclosed herein result in the preparation of high purity FDCA. The FDCA may have a purity of greater than about 80%, alternatively greater than about 85%, alternatively greater than about 95%, alternatively from about 80% to about 99%, alternatively from about 85% to about 99%, or alternatively from about 90% to about 99%.

ADDITIONAL DISCLOSURE

The following enumerated aspects of the present disclosures are provided as nonlimiting examples.

A first aspect which is a chemoenzymatic process for the preparation of 2,5-furan dicarboxylic acid, the process comprising contacting D-glucose with (i) at least two enzymes selected from the group consisting essentially of galactose oxidase, pyranose 2-oxidase, glucarate dehydratase, catalase, and a combination thereof to produce an intermediate; and (ii) contacting the intermediate with a metal catalyst and acid catalyst to form 2,5-furan dicarboxylic acid.

A second aspect which is the chemoenzymatic process of the first aspect wherein D-glucose is contacted with galactose oxidase and catalase to form D-glucodialdose; and wherein the process further comprises contacting D-glucodialdose with pyranose-2-oxidase and catalase under conditions suitable for the formation of 2-keto-glucodialdose; contacting 2-keto-glucodialdose with a heterogeneous metal catalyst to form 2-keto-glucaric acid; and dehydrating 2-ketoglucaric acid in the presence of an acid catalyst to form 2,5-furan dicarboxylic acid.

A third aspect which is the chemoenzymatic process of any of the first through second aspects wherein D-glucose is contacted with galactose oxidase and catalase to form D-glucodialdose; and wherein the process further comprises contacting D-glucodialdose with pyranose-2-oxidase and catalase under conditions suitable for the formation of 2-keto-glucodialdose; dehydrating 2-keto-glucodialdose with an acid catalyst to form 2,5-furandicaboxaldehyde; and oxidizing 2,5-furandicaboxaldehyde in the presence of a heterogeneous metal catalyst to form 2,5-furan dicarboxylic acid.

A fourth aspect which is the chemoenzymatic process of any of the first through third aspects, wherein D-glucose is contacted with galactose oxidase and catalase to form D-glucodialdose; and wherein the process further comprises contacting D-glucodialdose with a metal catalyst to form D-glucaric acid; dehydrating D-glucaric acid with glucarate dehydratase to form 5-keto-4-deoxy glucodialdose; and cyclizing 5-keto-4-deoxy glucodialdose in the presence of an acid catalyst to form 2,5-furan dicarboxylic acid.

A fifth aspect which is the chemoenzymatic process of any of the first through fourth aspects wherein D-glucose is contacted with pyranose-2-oxidase and catalase to form 2-keto-glucose; and wherein the process further comprises dehydrating 2-keto-glucose with an acid catalyst under conditions suitable for the formation of 2,5-furandicaboxaldehyde; dehydrating 5-keto-4-deoxyglucodialdose with an acid catalyst to form 2,5-furandicaboxaldehyde; and oxidizing 2,5-furandicaboxaldehyde in the presence of a heterogeneous metal catalyst to form 2,5-furan dicarboxylic acid.

A sixth aspect which is the chemoenzymatic process of any of the first through fifth aspects. wherein the galactose oxidase has any of SEQ ID NO.:1 to SEQ ID NO.:6.

A seventh aspect which is the chemoenzymatic process of the second aspect wherein the galactose oxidase has any of SEQ ID NO.:1 to SEQ ID NO.:6.

An eighth aspect which is the chemoenzymatic process of the third aspect wherein the galactose oxidase has any of SEQ ID NO.:1 to SEQ ID NO.:6.

A ninth aspect which is the chemoenzymatic process of the fourth aspect wherein the galactose oxidase has any of SEQ ID NO.:1 to SEQ ID NO.:6.

A tenth aspect which is the chemoenzymatic process of the fifth aspect, wherein the galactose oxidase has any of SEQ ID NO.:1 to SEQ ID NO.:6.

An eleventh aspect which is the chemoenzymatic process of any of the first through fifth aspects wherein the galactose oxidase has SEQ ID NO.:1.

A twelfth aspect which is the chemoenzymatic process of any of the first through eleventh aspects wherein the pyruvate-2-oxidase has any of SEQ ID NO.:7 to SEQ ID NO.:11.

A thirteenth aspect which is the chemoenzymatic process of any of the first through twelfth aspects carried out at a temperature of less than about 100° C.

A fourteenth aspect which is the chemoenzymatic process of any of the first through thirteenth aspects wherein the 2,5-furan dicarboxylic acid has a purity of greater than about 80%.

A fifteenth aspect which is the chemoenzymatic process of the second aspect wherein the 2,5-furan dicarboxylic acid has a purity of greater than about 80%.

A sixteenth aspect which is the chemoenzymatic process of the third aspect wherein the 2,5-furan dicarboxylic acid has a purity of greater than about 80%.

A seventeenth aspect which is the chemoenzymatic process of the fourth aspect wherein the 2,5-furan dicarboxylic acid has a purity of greater than about 80%.

An eighteenth aspect which is the chemoenzymatic process of the fifth aspect wherein the 2,5-furan dicarboxylic acid has a purity of greater than about 80%.

A nineteenth aspect which is the chemoenzymatic process of any of the first through eighteenth aspects wherein the heterogeneous metal catalyst comprises a support comprising carbon, silica, alumina, titania ($TiO_2$), zirconia ($ZrO_2$), zeolite, or any combination thereof.

A twentieth aspect which is the chemoenzymatic process of any of the first through nineteenth aspects wherein the acid catalyst, the metal catalyst or both are heterogeneous.

A twenty-first aspect which is the chemoenzymatic process of any of the first through twentieth aspects wherein the acid catalyst, the metal catalyst or both are homogeneous.

A twenty-second aspect which is a chemoenzymatic process for the preparation of 2,5-furan dicarboxylic acid, the process comprising enzymatic oxidation of 5-hydroxymethylfurfural using an enzymatic oxidizing composition comprising one or more enzymes selected from the group consisting of Aryl-alcohol oxidase (AAO) chloroperoxidase (CPO), 5-hydroxymethylfurfural oxidase (HMFO), glyoxal oxidase (GLOX), periplasmic aldehyde oxidase (PaoABC), unspecific peroxygenase (UPO), horseradish peroxidase (HRP), galactose oxidase (GAO) with and without the activating enzyme horseradish peroxidase (HRP), lactoperoxidase (LPO), myeloperoxidase (MPO), eosinophil peroxidase (EPO), thyroid peroxidase (TPO), ovoperoxidase, salivary peroxidase, vanadium haloperoxidase, non-mammalian vertebrate peroxidase (POX), peroxidasin (Pxd), bacterial peroxicin (Pxc), invertebrate peroxinectin (Pxt) and short peroxidockerin (PxDo), short peroxidockerin (Pxt), alpha-dioxygenase (aDox), dual oxidase (DuOx), prostaglandin H synthase or cyclooxygenase (PGHS/CyOx), linoleate diol synthase (LDS), functional variants thereof, and any combination thereof to form an intermediate; and oxidizing the intermediate using a metal catalyst to form 2,5-furan dicarboxylic acid.

A twenty-third aspect which is the chemoenzymatic process of the twenty-second aspect wherein the enzymatic oxidation is carried out at a temperature of less than about 100° C.

A twenty-fourth aspect which is the chemoenzymatic process of any of the twenty-second through twenty-third aspects wherein the 2,5-furan dicarboxylic acid has a purity of greater than about 80%.

A twenty-fifth aspect which is the chemoenzymatic process of any of the first through twenty-fourth aspects further comprising subjecting the 2,5-furan dicarboxylic to water crystallization, solvent crystallization, and Nutsche filtration.

EXAMPLES

The presently disclosed subject matter having been generally described, the following examples are given as particular aspects of the subject matter and to demonstrate the practice and advantages thereof. It is understood that the examples are given by way of illustration and are not intended to limit the specification or the claims in any manner.

Example 1

The specific activity of mutants from Table 1 on glucose were assessed and the results are presented in FIG. 1. Another GAO mutant capable of converting glucose to glucodialdose was engineered. Following directed evolution and rational enzyme engineering, the improved GAO mutant exhibits a specific activity of 35 U $mg^{-1}$ on glucose. Directed evolution of thirty sites within 10 Å of the catalytic copper was performed on a parent sequence containing the following added mutations: 1) R330, Q406T, W290F discovered by 2) C383S, and 3) Y405F and Q406E. Other mutations described in Table 4 were found to have neutral or deleterious effects on glucodialdose-generating activity. We named the new combination sequence GAO-Mut1. The full sequence of the expressed construct is given as SEQ ID No. 1, which contains a "MGHHHHHHSSGHIEGRHM" N-terminal his-tag and linker for expression and purification in *E. coli.*

Selected positions in GAO-Mut1 were mutated via the QUIKCHANGE method to all 20 amino acids using primers containing NNS codons. The constructs were then screened in the following manner: Colonies were picked and used to inoculate one well each in a 96-well deepwell plate charged with lysogeny broth (LB). The grown clones were then used to inoculate autoinduction media in a separate 96-well deepwell plate for protein expression. Harvested cells were lysed with Bacterial Protein Extraction Reagent (B-PER) and the lysate was then screened for oxidase activity using a colorimetric ABTS assay which detects hydrogen peroxide.

In short, lysate was assayed for activity with and without exposure to heat. To assay activity in the absence of a heat challenge, lysate was diluted 50 times. A volume of 5 μL of the diluted lysate was combined with ABTS assay solution (final concentration of 2% w/v glucose, 0.0125 mg/ml horseradish peroxidase, 50 mM sodium phosphate buffer at pH 8, 0.05% ABTS) to a final volume of 200 μL and the change in absorbance at 405 nm was monitored until the reaction was complete. To assay residual activity after a heat challenge, 50 μL lysate was incubated for ten minutes at 50° C. and 20 μL of the heat-treated lysate was added to the ABTS solution before monitoring change in absorbance at 405 nm. Specific activity was calculated from the formulas below using the linear portion of the curve to measure ΔA405/min and taking the extinction coefficient of ABTS at 405 nm as 36.8 $mM^{-1}$ $cm^{-1}$.

$$\text{Units mg}^{-1} = \frac{\Delta A_{405}\text{min}^{-1}}{36.8\times(\text{pathlength in cm})\times(\text{mg enzyme})/(\text{ml reaction mixture})}$$

$$\text{Units ml}^{-1} = \frac{\Delta A_{405}\text{min}^{-1}}{36.8\times(\text{pathlength in cm})\times(\text{ml enzyme})/(\text{ml reaction mixture})}$$

Mutant lysates exhibiting a ΔA405/min greater than GAO-Mut1 were chosen for further characterization. Following identification of the mutation by DNA sequencing, hits were expressed, purified, and assayed for specific activity and thermostability as assessed by the temperature at which one half maximal activity was observed ($T_{50}$). Mutants were purified from 5 ml culture with auto-induction medium in a 24 well plate. Harvested cells were lysed with B-PER and the lysate was spun down with 15,000 relative centrifugal force (rcf) for 30 min at 4° C. The lysate supernatant was used for protein purification with HisPur™ Ni-NTA Spin Plates. The eluted protein sample was diluted with 100 mM potassium phosphate buffer pH 7.5 with 0.5 mM $CuSO_4$, and specific activity was measured using the ABTS assay. $T_{50}$ was measured by heating protein in the absence of substrate, cooling, and then measuring residual activity using the ABTS assay. Heating was accomplished by diluting the protein to a concentration of 2.5 mg/L in a volume of 100 mM phosphate buffer at pH 7.5, aliquoting 50 μL into a row of a 96-well PCR plate, and incubating over a temperature gradient sufficient to capture maximal and minimal enzyme performance for ten minutes. Promptly after heating, the mixture was cooled on ice and the ΔA405/min of 20 μL of enzyme solution in 200 μL of final volume of ABTS solution was measured as described above.

Hits were purified, tested for activity and $T_{50}$, and recombined to generate a final best mutant from the directed evolution step. Promising point mutants that could beneficially be combined in the Mut F background included A193R D404H F441Y A72V are listed in Table 4. These mutations were combined into a single combination mutant named GAO-Mut47 which exhibited a specific activity of 27.3 U $mg^{-1}$ and a $T_{50}$ of 56.8° C. Table 3 provides a list of point mutations carried out and their characteristics.

TABLE 4

| Name | Mutations | U/mg | $T_{50}$ ° C. | $K_{cat}$ $S^{-1}$ | $K_m$ mM |
|---|---|---|---|---|---|
| M-RQW-S | | 1.1 | 56.8 | 31.4 | 2168.3 |
| GAO-mut1 | Y405F Q406E | 14.0 | 51.8 | 30.2 | 93.1 |
| GAO-mut6 | Y405F Q406E S383C | 6.1 | 41.5 | 36.6 | 412.0 |
| GAO-mut7 | Y405F Q406E F441Y | 16.9 | 53.6 | 27.3 | 42.7 |
| GAO-mut8 | Y405F Q406E D404H | 15.0 | 53.7 | 30.7 | 83.9 |
| GAO-mut9 | Y405F Q406E G461A | 13.4 | 53.2 | 27.8 | 83.7 |
| GAO-mut10 | Y405F Q406E I462R | 12.1 | 53.2 | 31.6 | 130.7 |
| GAO-mut11 | Y405F Q406E A172V | 21.2 | 48.5 | 39.5 | 72.6 |
| GAO-mut12 | Y405F Q406E A193R | 15.4 | 56.3 | 28.0 | 64.8 |
| GAO-mut13 | Y405F Q406E A193T | 14.6 | 53.8 | 30.4 | 75.5 |
| GAO-mut14 | Y405F Q406E D404H F441Y | 18.8 | 55.0 | 26.5 | 29.7 |
| GAO-mut15 | Y405F Q406E G461A I462R | 12.2 | 54.0 | 24.8 | 79.1 |
| GAO-mut17 | Y405F Q406E D404H F441Y G461A I462R | 18.2 | 55.3 | 23.6 | 25.5 |
| GAO-mut18 | Y405F Q406E A193T D404H F441Y G461A I462R | 18.1 | 56.6 | 24.1 | 28.0 |
| GAO-mut19 | Y405F Q406E A193T D404H F441Y G461A I462R S383C | 13.3 | 46.3 | 24.5 | 70.8 |
| GAO-mut20 | Y405F Q406E A193T D404H F441Y G461A I462R S383C A172V | 21.4 | 37.9 | 35.6 | 58.2 |
| GAO-mut21 | Y405F Q406E F441Y G461A I462R | 18.3 | 53.8 | 24.2 | 29.6 |
| GAO-mut22 | Y405F Q406E A193T D404H F441Y G461A I462R A172V | 23.6 | 51.5 | 29.5 | 26.4 |
| GAO-mut23 | Y405F Q406E A193R D404H F441Y G461A I462R A172V | 21.1 | 57.5 | 27.2 | 26.8 |
| GAO-mut47 | Y405F Q406E A193R D404H F441Y A172V | 27.3 | 56.8 | 35.0 | 25.2 |
| GAO-mut58 | Y405F Q406E D404H F441Y A172V | 27.1 | 52.9 | 35.4 | 26.6 |

Example 2

Figure 2:
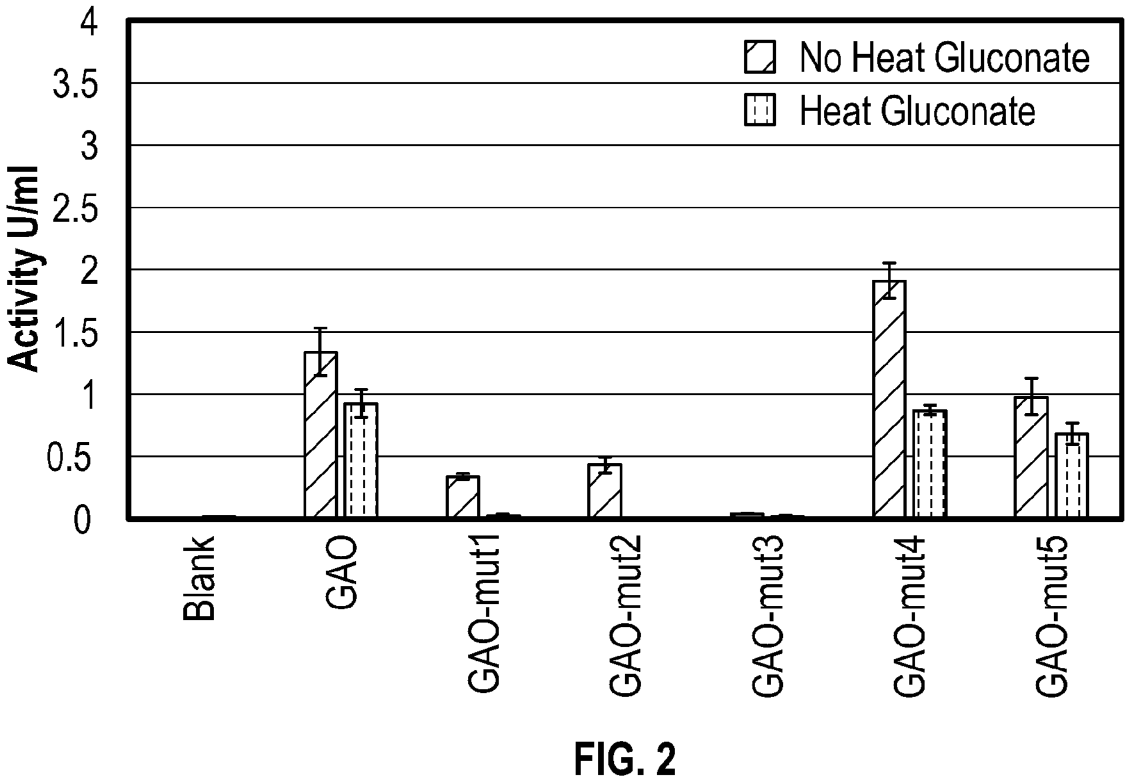
FIG. 2 is a graph of the specific activities for glucose and gluconate conversion for the samples from Example 2.

Rational engineering of GAO to further accept a glucose substrate and identify stabilizing mutations was accomplished with a combination of computational methods based on structural and multiple sequence alignment data (MSA). It was identified that GAO-M-RQW-S could accept both glucose and gluconate as substrate, the results are displayed in FIG. 2. Rational design was performed on the GAO-M-RQW-S sequence rather than GAO-Mut1. Structural methods employed included applying FoldX55 (40 predicted mutations) and PROSS56 (80 mutations) to a modified form of the Protein Database (PDB) structure 2WQ8 to contain the GAO-M-RQW-S mutations. MSA-based predictions were applied to a 185-member MSA. This MSA was generated from an initial set of 1000 sequences curated with JALVIEW to remove sequences with 98% redundancy and retain only sequences experimentally verified as carbohydrate oxidases. 30 mutations identified in designing a GAO for synthesizing an intermediate of the HIV drug Islatravir were also added to the panel.

Figure 3:
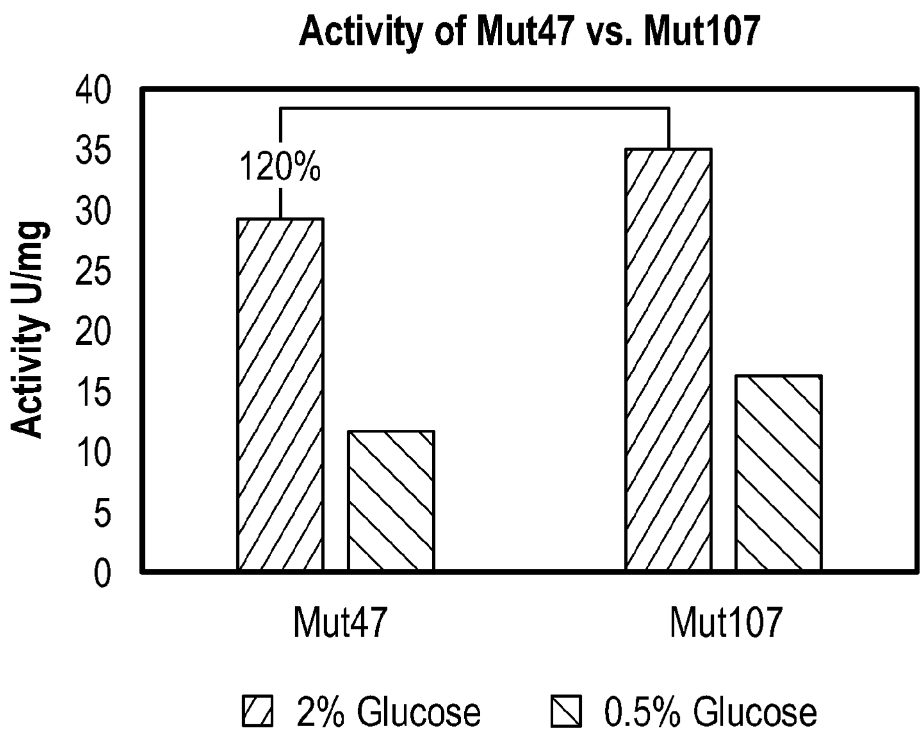
FIG. 3 is a graph of the activity of GAO-Mut47 and GAO-Mut107 on 0.5 and 2% glucose.

In total, 202-point mutants were screened using the same methods described above for screening the directed evolution clones. Thirty-nine hits were identified from an initial screen and sixteen were reidentified from a second round of screening. Upon generation of combo mutants in the best combination mutant from the directed evolution step (GAO-Mut47), the mutations N66S, S306A, S311F, and Q486L were identified as complementary and beneficial while N28I, Y189W, S331R, A378D, and R459Q were deemed detrimental in this background. The results are summarized in Table 5. The final GAO-Mut107 construct containing the Mut47 mutations and N66S, S306A, S311F, and Q486L exhibits a specific activity of 34.96 U $mg^{-1}$ on 2% glucose and a $T_{50}$ of 60.56° C. as shown in FIG. 3. Additional mutations identified from machine learning algorithms were later incorporated to generate GAO-mut142 and GAO-mut164.

TABLE 5

| Clone | Mutations from Mut47 | New Mutations | U/mg | Fold Improvement | T50 ° C. |
|---|---|---|---|---|---|
| Mut47 | | | 31.11 | 1.00 | 57.64 |
| GAO-mut68 | N28I | N28I | 30.84 | 0.99 | 56.76 |
| GAO-mut69 | N28I N66S | N66S | 33.68 | 1.08 | 59.00 |
| GAO-mut70 | N28I N66S Y189W | Y189W | 31.80 | 1.02 | 59.91 |
| GAO-mut71 | N28I N66S Y189W S306A | S306A | 32.66 | 1.05 | 59.48 |
| GAO-mut72 | N28I N66S Y189W S306A S311F | S311F | 33.87 | 1.09 | 60.81 |
| GAO-mut73 | N28I N66S Y189W S306A S311F S331R | S331R | 27.56 | 0.89 | 59.87 |
| GAO-mut74 | N28I N66S Y189W S306A S311F S331R A378D | A378D | 25.57 | 0.82 | 58.94 |
| GAO-mut75 | N28I N66S Y189W S306A S311F S331R A378D R459Q | R459Q | 23.51 | 0.76 | 58.49 |
| GAO-mut76 | N28I N66S Y189W S306A S311F S331R A378D R459Q V477D | V477D | 19.22 | 0.62 | 59.17 |
| GAO-mut77 | N28I N66S Y189W S306A S311F S331R A378D R459Q V477D Q486L | Q486L | 24.57 | 0.79 | 59.88 |
| GAO-mut107[a] | N66S S306A S311F Q486L | Removed N28I, Y189W, S331R, A378D, R459Q, and V477D | 34.96 | 1.20 | 60.56 |
| GAO-mut142[b] | N66S S306A S311F Q486L H40C | H40C | 37.53 | 1.29 | 58.76 |
| GAO-mut164[b] | N66S S306A S311F Q486L H40C L71C | L71C | 38.22 | 1.32 | 52.97 |

Bolded mutations are beneficial in a Mut47 background A193R D404H F441Y A172V

[a]Data collected in a separate experiment from other data. Fold improvement is calculated compared to an internal Mut47 control.

[b]Data collected in a separate experiment from other data. Fold improvement is calculated compared to an internal Mut47 control.

Example 3

Figure 4:
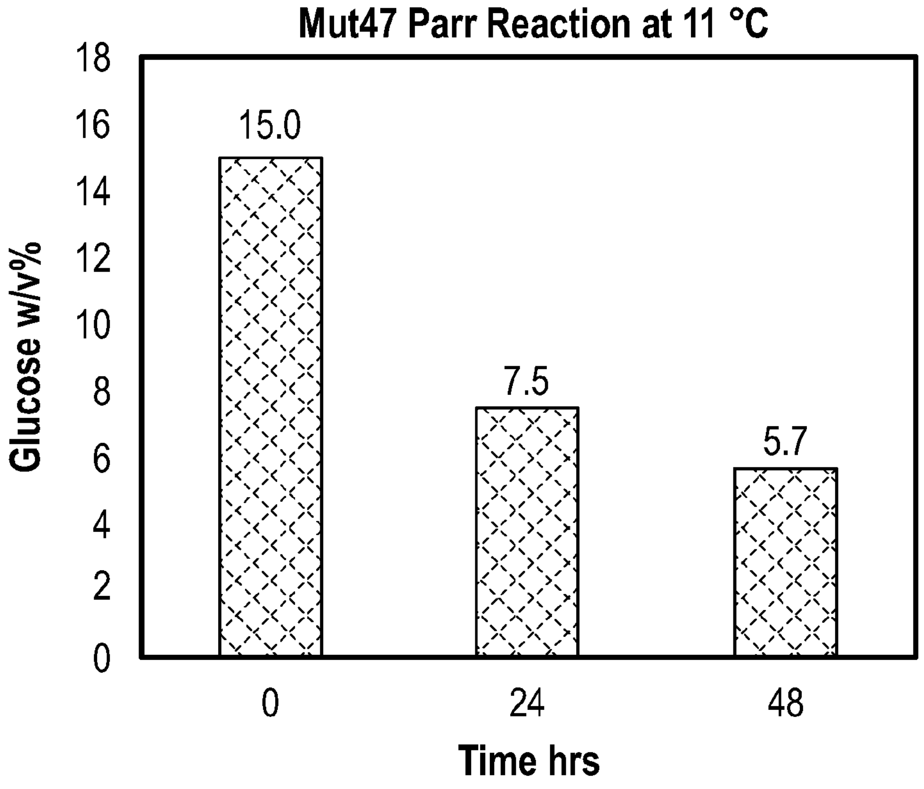
FIG. 4 is a plot of the residual glucose concentration in a Parr reaction.

A 50 ml reaction was conducted in a 200 mL vessel pressurized to 100 psi. The vessel was charged with 50 mM sodium phosphate pH 8 buffer, 50 μM $CuSO_4$, 15 w/v % glucose, 0.005 w/v % catalase, 0.001% horseradish peroxidase, and 0.001 w/v % engineered GAO. The reaction was stirred 500 rpm, 11° C. for 48 hours. Samples were taken at 0, 24, and 48 hours then assayed with HPLC to measure residual glucose and the results are presented in FIG. 4. The amount of starting material declined over 48 hours from 15 to 5.7% (w/v).

Example 4

Production of 2-Keto-Glucodialdose from Glucodialdose Via POX

To determine how POX might transform either D-glucose or D-glucodialdose to a product useful in the context of Scheme III, commercially available POX enzyme was obtained and used in a colorimetric 2,2'-azino-bis(3-ethylbenzothiazoline-6-sulphonic acid) (ABTS) reaction with either D-glucose, D-glucodialdose, 2-keto-D-gluconate, 2-keto-D-glucose, or 5-keto-D-glucose at a concentration of 20 mM in 50 mM pH 6 potassium phosphate buffer, at room temperature. Glucose oxidase (GOX) which is known to oxidize glucose at the C1 position to gluconolactone and GAO mutants were included in the assay as controls. In short, a 4× stock solution was prepared and diluted to a final reaction concentration of 20 mM substrate, 0.025 mg/ml horseradish peroxidase (HRP), 50 mM potassium phosphate buffer, pH 6, and 0.1% (w/v) ABTS. This solution was combined with enzyme to a final concentration of 0.8 μg/mL to begin the reaction and incubated for 25 minutes while monitoring A405 in a microtiter plate reader. Specific activity was calculated as:

$$\text{Units mg}^{-1} = \frac{\Delta A_{405}\text{min}^{-1}}{36.8\times(\text{pathlength in cm})\times(\text{mg enzyme})/(\text{ml reaction mixture})}$$

$$\text{Units ml}^{-1} = \frac{\Delta A_{405}\text{min}^{-1}}{36.8\times(\text{pathlength in cm})\times(\text{ml enzyme})/(\text{ml reaction mixture})}$$

Figure 5:
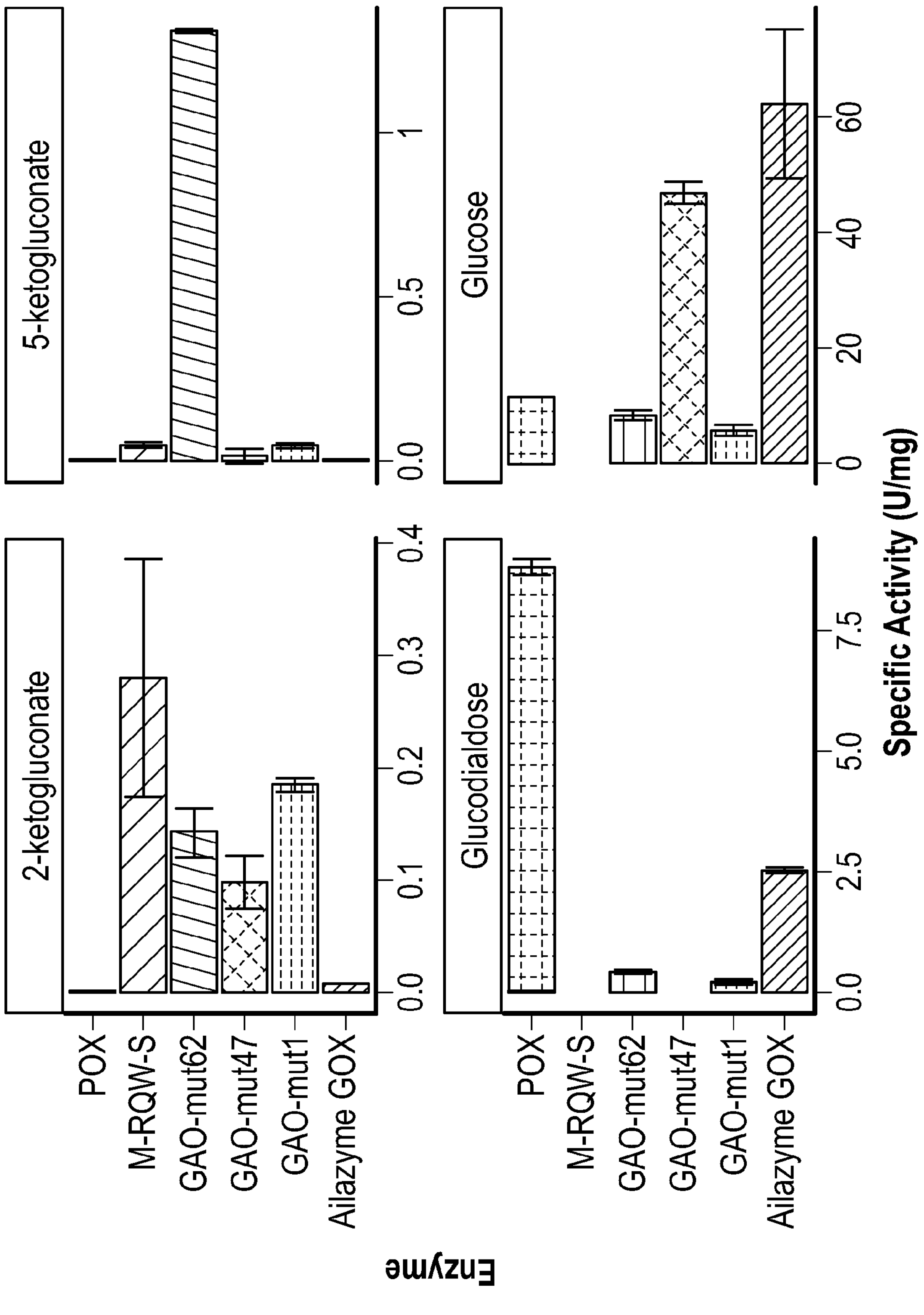
FIG. 5 is a plot of the specific activity of oxidizing enzymes on glucose and oxidized derivatives.

The results of the activity screen demonstrate the potential of using POX to generate 2-keto-glucodialdose from glucodialdose. POX exhibits 8.8 U/mg specific activity on glucodialdose (77% of performance on the native glucose substrate). This specific activity could be improved upon through engineering. The results are shown in Table 6 and FIG. 5. 2-ketoglucose, 2-ketogluconate, and 5-ketogluconate were not substrates for POX. None of the GAO enzymes were active on 2-keto-glucose. Given this data, production of 2-keto-glucodialdose should be possible in a dual reactor system where substrate passes through a first reactor charged with GAO to produce glucodialdose, then through a second reactor charged with POX to generate 2-keto-glucodialdose. Production via a single enzyme oxidation reactor will require engineering a GAO capable of accepting 2-keto-glucodialdose as a substrate. As expected, GOX exhibited high activity on the native substrate glucose.

TABLE 6

| Enzyme | Glucose (U $mg^{-1}$) | Glucodialdose (U $mg^{-1}$) | 2-ketoglucose (U $mg^{-1}$) | 2-ketogluconate (U $mg^{-1}$) | 5-ketogluconate (U $mg^{-1}$) |
|---|---|---|---|---|---|
| GAO-mut1 | 5.7 | 0.2 | 0.0 | 0.2 | 0.0 |
| GAO-mut47 | 46.9 | n.d. | 0.0 | 0.1 | 0.0 |
| GAO-mut62 | 8.3 | 0.4 | 0.0 | 0.1 | 1.3 |
| M-RQW-S | n.d | n.d. | 0.0 | 0.3 | 0.0 |
| GOX | 62.2 | 2.5 | 0.0 | 0.0 | 0.0 |
| POX | 11.4 | 8.8 | 0.0 | 0.0 | 0.0 |

The product profile was probed through HPLC-MS. A 50 μL reaction in a 96-well microtiter plate containing 0.1% (w/v) POX, 10% (w/v) substrate, 0.005% (w/v) catalase, and 80 mM potassium phosphate buffer at pH 6.0 was analyzed using the following method: Mobile Phase A: 50 mM Ammonium Formate+1% Formic Acid in Water Mobile Phase B: 1% Formic Acid in Acetonitrile Column Temp: 50 C Column: Torus 2-Pic 1.7 μm, 3.0 mm×150 mm, Selected Ion Monitoring: 173, 175, 177, 179, 193, and 195 was done, Cone Voltages: Default values The timed method is presented in Table 7.

TABLE 7

| Time | Flow (mL/min) | % A | % B |
|---|---|---|---|
| 0 | 0.8 | 30 | 70 |
| 3 | 0.8 | 80 | 20 |
| 4 | 0.8 | 80 | 20 |
| 5 | 0.8 | 30 | 70 |
| 5.1 | 0.8 | 30 | 70 |
| 7 | 0.8 | 30 | 70 |

Figure 6:
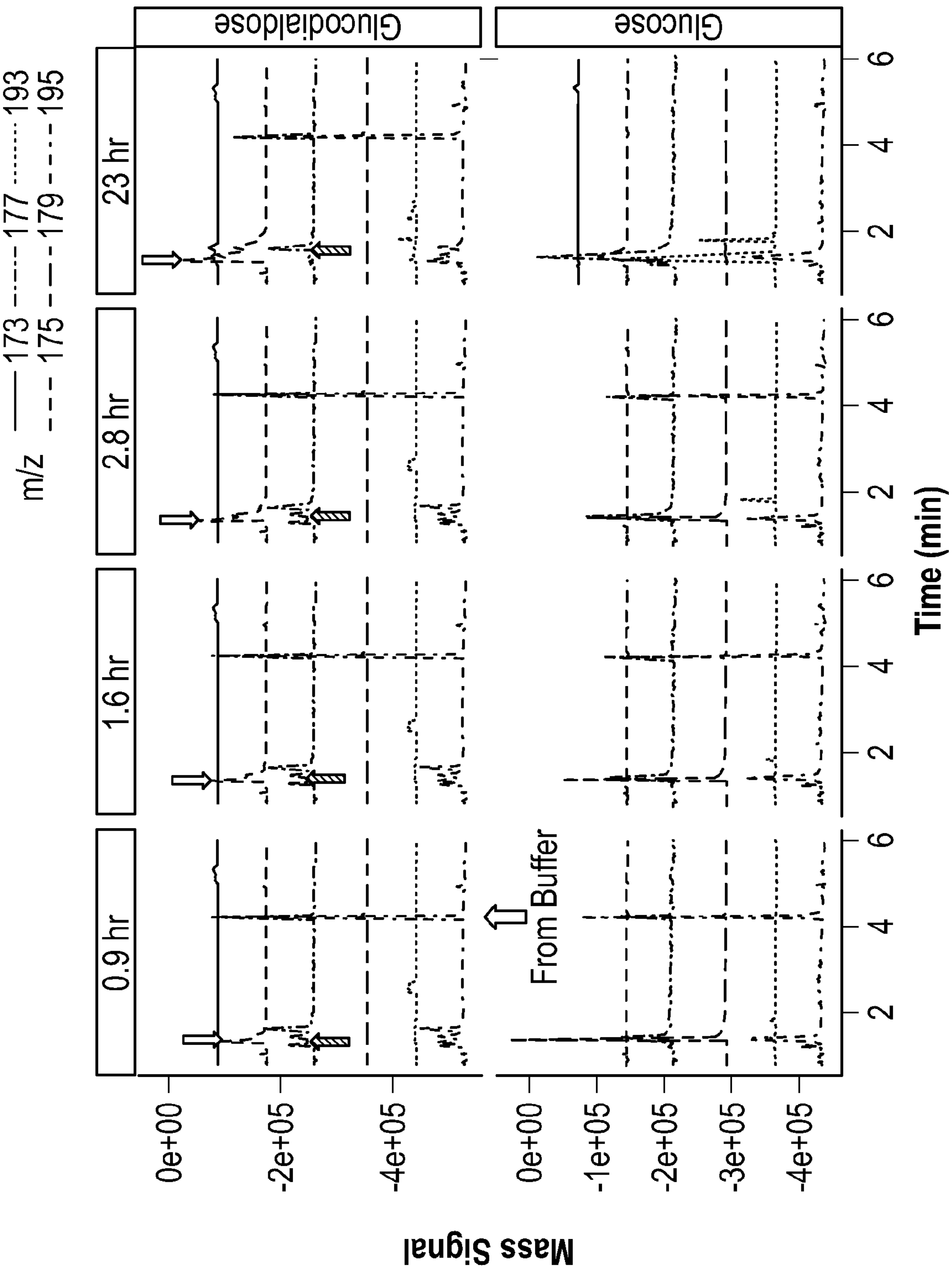
FIG. 6 is a compilation of HPLC-MS traces of pyranose 2-oxidase in glucodialdose or glucose reactions.

A peak in the 175 m/z channel corresponding to the expected 2-keto-glucodialdose product was detected as early as 54 minutes and continued to grow in accordance with disappearance of glucodialdose (177 m/z). These results are presented in FIG. 6. Mass channels in negative ion mode from top to bottom correspond to 173, 175, 177, 179, 193, 195 m/z. The 173 m/z channel is not shown for the glucose 0.9, 1.6, or 2.8 hr reactions.

Glucodialdose typical exhibits three peaks in the 177 m/z channel potentially corresponding to different cyclized forms of the compound. It is curious that the glucodialdose peak with the longest retention time disappears more slowly than the others suggesting POX may prefer some configurations of the substrate over others. Some peaks appear in the 193 m/z channel which could correspond to glucuronic or glucuronic acid.

While aspects of the presently disclosed subject matter have been shown and described, modifications thereof can be made by one skilled in the art without departing from the spirit and teachings of the subject matter. The aspects described herein are exemplary only, and are not intended to be limiting. Many variations and modifications of the subject matter disclosed herein are possible and are within the scope of the disclosed subject matter. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term “optionally” with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the aspects of the present invention. The discussion of a reference herein is not an admission that it is prior art to the presently disclosed subject matter, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A chemoenzymatic process for the preparation of 2,5-furan dicarboxylic acid, the process comprising:

contacting D-glucose with galactose oxidase having an amino acid sequence of any of SEQ ID NO.: 1 to SEQ ID NO.: 6 and catalase to form D-glucodialdose;

contacting the D-glucodialdose with pyranose-2-oxidase having an amino acid sequence of any of SEQ ID NO:7 to SEQ ID NO.:11 and catalase under conditions suitable for the formation of 2-keto-glucodialdose;

contacting the 2-keto-glucodialdose or an intermediate with a metal catalyst and acid catalyst to form 2,5-furan dicarboxylic acid, wherein the metal catalyst comprises gold, platinum, ruthenium, palladium, iridium, osmium, rhodium, rhenium, silver, or combinations thereof, and wherein the acid catalyst comprises an ion exchange resin, sulfonated silica, a zeolite, niobium oxide, a mineral acid, or a combination thereof.

2. The chemoenzymatic process of claim 1, wherein the process further comprises:

contacting the 2-keto-glucodialdose with a heterogeneous metal catalyst to form 2-keto-glucaric acid as the intermediate; and dehydrating 2-ketoglucaric acid in the presence of an acid catalyst to form 2,5-furan dicarboxylic acid.

3. The chemoenzymatic process of claim 1, wherein the process further comprises:

dehydrating the 2-keto-glucodialdose with an acid catalyst to form 2.5-furandicarboxaldehyde as the intermediate; and oxidizing 2.5-furandicaboxaldehyde in the presence of a heterogeneous metal catalyst to form 2,5-furan dicarboxylic acid.

4. The chemoenzymatic process of claim 1, wherein the galactose oxidase has an amino acid sequence of SEQ ID NO.: 1.

5. The chemoenzymatic process of claim 1, carried out at a temperature of less than about 100° C.

6. The chemoenzymatic process of claim 1, wherein the 2,5-furan dicarboxylic acid has a purity of greater than about 80%.

7. The chemoenzymatic process of claim 2, wherein the 2,5-furan dicarboxylic acid has a purity of greater than about 80%.

8. The chemoenzymatic process of claim 3, wherein the 2,5-furan dicarboxylic acid has a purity of greater than about 80%.

9. The chemoenzymatic process of claim 1, wherein the metal catalyst comprises a heterogeneous metal catalyst comprising a support comprising carbon, silica, alumina, titania ($TiO_2$), zirconia ($ZrO_2$), zeolite, or any combination thereof.

10. The chemoenzymatic process of claim 1, wherein the acid catalyst, the metal catalyst or both are heterogeneous.

11. The chemoenzymatic process of claim 1, wherein the acid catalyst, the metal catalyst or both are homogeneous.

12. The chemoenzymatic process of claim 1 further comprising subjecting the 2,5-furan dicarboxylic acid to water crystallization, solvent crystallization, and Nutsche filtration.

13. The chemoenzymatic process of claim 1, wherein the pyranose-2-oxidase has an amino acid sequence of SEQ ID NO.: 7.

14. The chemoenzymatic process of claim 1, wherein the metal catalyst comprises gold.

15. The chemoenzymatic process of claim 1, wherein the contacting with galactose oxidase and the contacting with pyranose-2-oxidase are each carried out at a temperature ranging from about 20° C. to about 60° C.

16. The chemoenzymatic process of claim 1, wherein the 2,5-furan dicarboxylic acid has a purity of greater than about 95%.

* * * * *

SEQUENCE LISTING

<160> NUMBER OF SEQ ID NOS: 11

<210> SEQ ID NO 1
<211> LENGTH: 639
<212> TYPE: PRT
<213> ORGANISM: Artificial Sequence
<220> FEATURE:
<223> OTHER INFORMATION: mutated fragment from wildtype Fusarium graminearum

<400> SEQUENCE: 1

Ala Ser Ala Pro Ile Gly Ser Ala Ile Pro Arg Asn Asn Trp Ala Val
1 5 10 15

Thr Cys Asp Ser Ala Gln Ser Gly Asn Glu Cys Asn Lys Ala Ile Asp
20 25 30

Gly Asn Lys Asp Thr Phe Trp His Thr Phe Tyr Gly Ala Asn Gly Asp
35 40 45

Pro Lys Pro Pro His Thr Tyr Thr Ile Asp Met Lys Thr Thr Gln Asn
50 55 60

Val Asn Gly Leu Ser Val Leu Pro Arg Gln Asp Gly Asn Gln Asn Gly
65 70 75 80

Trp Ile Gly Arg His Glu Val Tyr Leu Ser Ser Asp Gly Thr Asn Trp
85 90 95

Gly Ser Pro Val Ala Ser Gly Ser Trp Phe Ala Asp Ser Thr Thr Lys
100 105 110

Tyr Ser Asn Phe Glu Thr Arg Pro Ala Arg Tyr Val Arg Leu Val Ala
115 120 125

Ile Thr Glu Ala Asn Gly Gln Pro Trp Thr Ser Ile Ala Glu Ile Asn
130 135 140

Val Phe Gln Ala Ser Ser Tyr Thr Ala Pro Gln Pro Gly Leu Gly Arg
145 150 155 160

Trp Gly Pro Thr Ile Asp Leu Pro Ile Val Pro Ala Ala Ala Ala Ile
165 170 175

Glu Pro Thr Ser Gly Arg Val Leu Met Trp Ser Ser Tyr Arg Asn Asp
180 185 190

Ala Phe Glu Gly Ser Pro Gly Gly Ile Thr Leu Thr Ser Ser Trp Asp
195 200 205

Pro Ser Thr Gly Ile Val Ser Asp Arg Thr Val Thr Val Thr Lys His
210 215 220

Asp Met Phe Cys Pro Gly Ile Ser Met Asp Gly Asn Gly Gln Ile Val
225 230 235 240

Val Thr Gly Gly Asn Asp Ala Lys Lys Thr Ser Leu Tyr Asp Ser Ser
245 250 255

-continued

```
Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
        275                 280                 285

Ser Phe Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Lys Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Ser Gly
    370                 375                 380

Asn Ala Val Met Tyr Asp Ala Val Lys Gly Lys Ile Leu Thr Phe Gly
385                 390                 395                 400

Gly Ser Pro Asp Tyr Thr Asp Ser Asp Ala Thr Thr Asn Ala His Ile
                405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
        435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asp Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635
```

```
<210> SEQ ID NO 2
<211> LENGTH: 639
<212> TYPE: PRT
<213> ORGANISM: Artificial Sequence
<220> FEATURE:
```

-continued

<223> OTHER INFORMATION: mutated fragment from wildtype Fusarium graminearum

<400> SEQUENCE: 2

```
Ala Ser Ala Pro Ile Gly Ser Ala Ile Pro Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
        35                  40                  45

Pro Lys Pro Pro His Thr Tyr Thr Ile Asp Met Lys Thr Thr Gln Asn
    50                  55                  60

Val Asn Gly Leu Ser Val Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125

Ile Thr Glu Ala Asn Gly Gln Pro Trp Thr Ser Ile Ala Glu Ile Asn
    130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
            180                 185                 190

Ala Phe Glu Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
    210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
        275                 280                 285

Ser Phe Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Lys Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Ser Gly
    370                 375                 380

Asn Ala Val Met Tyr Asp Ala Val Lys Gly Lys Ile Leu Thr Phe Gly
385                 390                 395                 400
```

```
Gly Ser Pro Asp Phe Glu Asp Ser Asp Ala Thr Thr Asn Ala His Ile
                405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
        435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asp Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635


<210> SEQ ID NO 3
<211> LENGTH: 639
<212> TYPE: PRT
<213> ORGANISM: Artificial Sequence
<220> FEATURE:
<223> OTHER INFORMATION: mutated fragment from wildtype Fusarium
      graminearum

<400> SEQUENCE: 3

Ala Ser Ala Pro Ile Gly Ser Ala Ile Pro Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
        35                  40                  45

Pro Lys Pro Pro His Thr Tyr Thr Ile Asp Met Lys Thr Thr Gln Asn
    50                  55                  60

Val Asn Gly Leu Ser Val Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
```

-continued

```
        115                 120                 125

Ile Thr Glu Ala Asn Gly Gln Pro Trp Thr Ser Ile Ala Glu Ile Asn
    130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Val Ala Ala Ala Ile
                165                 170                 175

Glu Pro Thr Ser Gly Arg Val Leu Met Trp Ser Ser Tyr Arg Asn Asp
            180                 185                 190

Arg Phe Glu Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
    210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
        275                 280                 285

Ser Phe Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Lys Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Ser Gly
    370                 375                 380

Asn Ala Val Met Tyr Asp Ala Val Lys Gly Lys Ile Leu Thr Phe Gly
385                 390                 395                 400

Gly Ser Pro His Phe Glu Asp Ser Asp Ala Thr Thr Asn Ala His Ile
                405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Tyr His Thr Ser Val Val Leu Pro
        435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asp Ser Asn Gly Asn Leu Ala Thr Arg Pro
    530                 535                 540
```

```
Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635


<210> SEQ ID NO 4
<211> LENGTH: 639
<212> TYPE: PRT
<213> ORGANISM: Artificial Sequence
<220> FEATURE:
<223> OTHER INFORMATION: mutated fragment from wildtype Fusarium
      graminearum

<400> SEQUENCE: 4

Ala Ser Ala Pro Ile Gly Ser Ala Ile Pro Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
        35                  40                  45

Pro Lys Pro Pro His Thr Tyr Thr Ile Asp Met Lys Thr Thr Gln Asn
    50                  55                  60

Val Ser Gly Leu Ser Val Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125

Ile Thr Glu Ala Asn Gly Gln Pro Trp Thr Ser Ile Ala Glu Ile Asn
    130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Val Ala Ala Ala Ile
                165                 170                 175

Glu Pro Thr Ser Gly Arg Val Leu Met Trp Ser Ser Trp Arg Asn Asp
            180                 185                 190

Ala Phe Glu Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
    210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
```

```
            260                 265                 270

Gln Ser Ser Ala Thr Met Ser Asp Gly Arg Val Phe Thr Ile Gly Gly
        275                 280                 285

Ser Phe Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Lys Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Ser Gly
    370                 375                 380

Asn Ala Val Met Tyr Asp Ala Val Lys Gly Lys Ile Leu Thr Phe Gly
385                 390                 395                 400

Gly Ser Pro Asp Tyr Thr Asp Ser Asp Ala Thr Thr Asn Ala His Ile
                405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
        435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asp Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635


<210> SEQ ID NO 5
<211> LENGTH: 639
<212> TYPE: PRT
<213> ORGANISM: Artificial Sequence
<220> FEATURE:
<223> OTHER INFORMATION: mutated fragment from wildtype Fusarium
      graminearum
```

-continued

<400> SEQUENCE: 5

Ala Ser Ala Pro Ile Gly Ser Ala Ile Pro Arg Asn Asn Trp Ala Val
1 5 10 15

Thr Cys Asp Ser Ala Gln Ser Gly Asn Glu Cys Asn Lys Ala Ile Asp
20 25 30

Gly Asn Lys Asp Thr Phe Trp His Thr Phe Tyr Gly Ala Asn Gly Asp
35 40 45

Pro Lys Pro Pro His Thr Tyr Thr Ile Asp Met Lys Thr Thr Gln Asn
50 55 60

Val Ser Gly Leu Ser Val Leu Pro Arg Gln Asp Gly Asn Gln Asn Gly
65 70 75 80

Trp Ile Gly Arg His Glu Val Tyr Leu Ser Ser Asp Gly Thr Asn Trp
85 90 95

Gly Ser Pro Val Ala Ser Gly Ser Trp Phe Ala Asp Ser Thr Thr Lys
100 105 110

Tyr Ser Asn Phe Glu Thr Arg Pro Ala Arg Tyr Val Arg Leu Val Ala
115 120 125

Ile Thr Glu Ala Asn Gly Gln Pro Trp Thr Ser Ile Ala Glu Ile Asn
130 135 140

Val Phe Gln Ala Ser Ser Tyr Thr Ala Pro Gln Pro Gly Leu Gly Arg
145 150 155 160

Trp Gly Pro Thr Ile Asp Leu Pro Ile Val Pro Val Ala Ala Ala Ile
165 170 175

Glu Pro Thr Ser Gly Arg Val Leu Met Trp Ser Ser Trp Arg Asn Asp
180 185 190

Ala Phe Glu Gly Ser Pro Gly Gly Ile Thr Leu Thr Ser Ser Trp Asp
195 200 205

Pro Ser Thr Gly Ile Val Ser Asp Arg Thr Val Thr Val Thr Lys His
210 215 220

Asp Met Phe Cys Pro Gly Ile Ser Met Asp Gly Asn Gly Gln Ile Val
225 230 235 240

Val Thr Gly Gly Asn Asp Ala Lys Lys Thr Ser Leu Tyr Asp Ser Ser
245 250 255

Ser Asp Ser Trp Ile Pro Gly Pro Asp Met Gln Val Ala Arg Gly Tyr
260 265 270

Gln Ser Ser Ala Thr Met Ser Asp Gly Arg Val Phe Thr Ile Gly Gly
275 280 285

Ser Phe Ser Gly Gly Val Phe Glu Lys Asn Gly Glu Val Tyr Ser Pro
290 295 300

Ser Ala Lys Thr Trp Thr Phe Leu Pro Asn Ala Lys Val Asn Pro Met
305 310 315 320

Leu Thr Ala Asp Lys Gln Gly Leu Tyr Lys Arg Asp Asn His Ala Trp
325 330 335

Leu Phe Gly Trp Lys Lys Gly Ser Val Phe Gln Ala Gly Pro Ser Thr
340 345 350

Ala Met Asn Trp Tyr Tyr Thr Ser Gly Ser Gly Asp Val Lys Ser Ala
355 360 365

Gly Lys Arg Gln Ser Asn Arg Gly Val Asp Pro Asp Ala Met Ser Gly
370 375 380

Asn Ala Val Met Tyr Asp Ala Val Lys Gly Lys Ile Leu Thr Phe Gly
385 390 395 400

Gly Ser Pro Asp Tyr Thr Asp Ser Asp Ala Thr Thr Asn Ala His Ile

-continued

```
                405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
        435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Leu Asn Pro Asn Ser Ile Val Arg Ala Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asp Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635


<210> SEQ ID NO 6
<211> LENGTH: 638
<212> TYPE: PRT
<213> ORGANISM: Artificial Sequence
<220> FEATURE:
<223> OTHER INFORMATION: mutated fragment from wildtype Fusarium
      graminearum

<400> SEQUENCE: 6

Ala Ser Ala Pro Ile Gly Ser Ala Ile Pro Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Pro
        35                  40                  45

Lys Pro Pro His Thr Tyr Thr Ile Asp Met Lys Thr Thr Gln Asn Val
    50                  55                  60

Ser Gly Leu Ser Val Leu Pro Arg Gln Asp Gly Asn Gln Asn Gly Trp
65                  70                  75                  80

Ile Gly Arg His Glu Val Tyr Leu Ser Ser Asp Gly Thr Asn Trp Gly
                85                  90                  95

Ser Pro Val Ala Ser Gly Ser Trp Phe Ala Asp Ser Thr Thr Lys Tyr
            100                 105                 110

Ser Asn Phe Glu Thr Arg Pro Ala Arg Tyr Val Arg Leu Val Ala Ile
        115                 120                 125
```

-continued

```
Thr Glu Ala Asn Gly Gln Pro Trp Thr Ser Ile Ala Glu Ile Asn Val
    130                 135                 140

Phe Gln Ala Ser Ser Tyr Thr Ala Pro Gln Pro Gly Leu Gly Arg Trp
145                 150                 155                 160

Gly Pro Thr Ile Asp Leu Pro Ile Val Pro Val Ala Ala Ala Ile Glu
                165                 170                 175

Pro Thr Ser Gly Arg Val Leu Met Trp Ser Ser Tyr Arg Asn Asp Arg
            180                 185                 190

Phe Glu Gly Ser Pro Gly Gly Ile Thr Leu Thr Ser Ser Trp Asp Pro
        195                 200                 205

Ser Thr Gly Ile Val Ser Asp Arg Thr Val Thr Val Thr Lys His Asp
    210                 215                 220

Met Phe Cys Pro Gly Ile Ser Met Asp Gly Asn Gly Gln Ile Val Val
225                 230                 235                 240

Thr Gly Gly Asn Asp Ala Lys Lys Thr Ser Leu Tyr Asp Ser Ser Ser
                245                 250                 255

Asp Ser Trp Ile Pro Gly Pro Asp Met Gln Val Ala Arg Gly Tyr Gln
            260                 265                 270

Ser Ser Ala Thr Met Ser Asp Gly Arg Val Phe Thr Ile Gly Gly Ser
        275                 280                 285

Phe Ser Gly Gly Val Phe Glu Lys Asn Gly Glu Val Tyr Ser Pro Ser
    290                 295                 300

Ala Lys Thr Trp Thr Phe Leu Pro Asn Ala Lys Val Asn Pro Met Leu
305                 310                 315                 320

Thr Ala Asp Lys Gln Gly Leu Tyr Lys Ser Asp Asn His Ala Trp Leu
                325                 330                 335

Phe Gly Trp Lys Lys Gly Ser Val Phe Gln Ala Gly Pro Ser Thr Ala
            340                 345                 350

Met Asn Trp Tyr Tyr Thr Ser Gly Ser Gly Asp Val Lys Ser Ala Gly
        355                 360                 365

Lys Arg Gln Ser Asn Arg Gly Val Ala Pro Asp Ala Met Ser Gly Asn
    370                 375                 380

Ala Val Met Tyr Asp Ala Val Lys Gly Lys Ile Leu Thr Phe Gly Gly
385                 390                 395                 400

Ser Pro His Phe Glu Asp Ser Asp Ala Thr Thr Asn Ala His Ile Ile
                405                 410                 415

Thr Leu Gly Glu Pro Gly Thr Ser Pro Asn Thr Val Phe Ala Ser Asn
            420                 425                 430

Gly Leu Tyr Phe Ala Arg Thr Tyr His Thr Ser Val Val Leu Pro Asp
        435                 440                 445

Gly Ser Thr Phe Ile Thr Gly Gly Gln Arg Arg Gly Ile Pro Phe Glu
    450                 455                 460

Asp Ser Thr Pro Val Phe Thr Pro Glu Ile Tyr Val Pro Glu Gln Asp
465                 470                 475                 480

Thr Phe Tyr Lys Gln Asn Pro Asn Ser Ile Val Arg Ala Tyr His Ser
                485                 490                 495

Ile Ser Leu Leu Leu Pro Asp Gly Arg Val Phe Asn Gly Gly Gly Gly
            500                 505                 510

Leu Cys Gly Asp Cys Thr Thr Asn His Phe Asp Ala Gln Ile Phe Thr
        515                 520                 525

Pro Asn Tyr Leu Tyr Asp Ser Asn Gly Asn Leu Ala Thr Arg Pro Lys
    530                 535                 540

Ile Thr Arg Thr Ser Thr Gln Ser Val Lys Val Gly Gly Arg Ile Thr
```

-continued 545 550 555 560

Ile Ser Thr Asp Ser Ser Ile Ser Lys Ala Ser Leu Ile Arg Tyr Gly
565 570 575

Thr Ala Thr His Thr Val Asn Thr Asp Gln Arg Arg Ile Pro Leu Thr
580 585 590

Leu Thr Asn Asn Gly Gly Asn Ser Tyr Ser Phe Gln Val Pro Ser Asp
595 600 605

Ser Gly Val Ala Leu Pro Gly Tyr Trp Met Leu Phe Val Met Asn Ser
610 615 620

Ala Gly Val Pro Ser Val Ala Ser Thr Ile Arg Val Thr Gln
625 630 635

<210> SEQ ID NO 7
<211> LENGTH: 531
<212> TYPE: PRT
<213> ORGANISM: Pseudarthrobacter phenanthrenivorans

<400> SEQUENCE: 7

Met Ser Gly His Arg Tyr Pro Ala Ala Val Asp Val Ala Ile Val Gly
1 5 10 15

Ser Gly Pro Thr Ala Ser Ala Tyr Ala Arg Ile Leu Ser Glu Glu Ala
20 25 30

Pro Gly Ala Thr Ile Ala Met Phe Glu Val Gly Pro Thr Val Ser Ile
35 40 45

Pro Pro Gly Ala His Val Lys Asn Ile Glu Asp Pro Glu Arg Arg Ser
50 55 60

Ser Ala Gln Arg Ala Ser Glu Gly Pro Gly Ala Gly Ala Glu Thr Val
65 70 75 80

Ser Ser Pro Gly Ala Val Lys Ser Gly Glu Arg Arg Ala Arg Pro Gly
85 90 95

Thr Tyr Leu Leu Gln Asp Gly Tyr Ala Phe Pro Gly Glu Asp Gly Met
100 105 110

Pro Val Ala Ala Met Ser Ser Asn Val Gly Gly Met Ala Ala His Trp
115 120 125

Thr Ala Ala Cys Pro Arg Pro Gly Gly Lys Glu Arg Ile Pro Phe Leu
130 135 140

Pro Asp Leu Glu Asp Leu Leu Asp Asp Ala Asp Arg Leu Leu Gly Val
145 150 155 160

Thr Thr His Ala Phe Asp Gly Ala Pro Phe Ser Asp Leu Val Arg Glu
165 170 175

Arg Leu Ala Ala Val Val Asp Asn Gly Arg Gly Pro Ala Phe Arg Val
180 185 190

Gln Pro Met Pro Leu Ala Val His Arg Arg Glu Asp Gly Gly Leu Val
195 200 205

Trp Ser Gly Ser Asp Val Val Met Gly Asp Val Thr Arg Glu Asn Pro
210 215 220

Gln Phe His Leu Phe Asp Glu Ser Leu Val Thr Arg Val Leu Val Glu
225 230 235 240

Asp Gly Val Ala Ala Gly Val Glu Val Gln Asp Arg Arg Thr Gly Gly
245 250 255

Thr His Gln Val Ser Ala Arg Tyr Val Val Val Gly Ala Asp Ala Leu
260 265 270

Arg Thr Pro Gln Leu Leu Trp Ala Ser Gly Ile Arg Pro Asp Ala Leu
275 280 285

Gly Arg Tyr Leu Asn Asp Gln Ala Gln Val Val Phe Ala Ser Arg Leu
    290                 295                 300

Arg Gly Val Thr Ala Pro Gln Gly Ser Ala Ala Ala Asp Gly Ala Leu
305                 310                 315                 320

Ser Glu Gln Ser Gly Val Ala Trp Val Pro Tyr Thr Asp Glu Ala Pro
                325                 330                 335

Phe His Gly Gln Ile Met Gln Leu Asp Ala Ser Pro Val Pro Leu Ala
            340                 345                 350

Glu Asp Asp Pro Val Val Pro Gly Ser Ile Val Gly Leu Gly Leu Phe
        355                 360                 365

Cys Ala Lys Asp Leu Gln Arg Glu Asp Arg Val Ala Phe Asp Asp Gly
    370                 375                 380

Ala Arg Asp Ser Tyr Gly Met Pro Ala Met Arg Ile His Tyr Arg Leu
385                 390                 395                 400

Thr Glu Arg Asp Arg Glu Val Leu Glu Arg Ala Arg Gln Glu Ile Val
                405                 410                 415

Arg Leu Gly Lys Ala Val Gly Glu Pro Leu Asp Glu Gln Pro Phe Val
            420                 425                 430

Leu Pro Pro Gly Ala Ser Leu His Tyr Gln Gly Thr Thr Arg Met Ala
        435                 440                 445

Arg Thr Asp Asp Gly Glu Ser Val Cys Ser Pro Asp Ser Glu Val Trp
    450                 455                 460

Gln Val Pro Gly Leu Phe Val Ala Gly Asn Gly Val Ile Pro Thr Ala
465                 470                 475                 480

Thr Ala Cys Asn Pro Thr Leu Thr Ala Val Ala Leu Ala Val Arg Gly
                485                 490                 495

Ala Arg Lys Val Ala Glu Lys Leu Asn Ser Ser Leu Leu Met Ser Asn
            500                 505                 510

Ser Asp Asn Arg Val Ser Lys Gly Gly Ser Gly Ser Gly His His His
        515                 520                 525

His His His
    530

<210> SEQ ID NO 8
<211> LENGTH: 653
<212> TYPE: PRT
<213> ORGANISM: Irpex lacteus

<400> SEQUENCE: 8

Met Ser Asn Leu Pro Pro His Glu Ile His Ala Lys Thr Gly Ile Asn
1               5                   10                  15

Gln Phe Asp Val Phe Ile Ala Gly Ser Gly Pro Ile Gly Ala Thr Tyr
            20                  25                  30

Ala Arg Leu Leu Thr Arg His Gly Tyr Asn Val Ile Met Thr Glu Ile
        35                  40                  45

Gly Asp Gln Glu Thr Arg Val Pro Ala Ser His Lys Lys Asn Glu Ile
    50                  55                  60

Glu Tyr Gln Lys Asp Ile Asp Arg Phe Val Arg Val Ile Gln Gly Ala
65                  70                  75                  80

Leu Ser Thr Val Ser Val Pro Pro Ala Ser Thr Val Ile Pro Gln Leu
                85                  90                  95

Asp Pro Ser Ala Trp Arg Pro Glu Asp Pro Ser Gln Met Thr Leu Leu
            100                 105                 110

Asn Gly Arg Asn Pro Asn Gln Gln Thr Tyr Asp Asn Leu Pro Ala Glu
        115                 120                 125

-continued

Ser Val Thr Arg Cys Val Gly Gly Met Ser Thr His Trp Thr Cys Ala
    130                 135                 140

Thr Pro Glu Phe Phe Lys Glu Asn Gly Glu Arg Pro Lys Ile Phe Pro
145                 150                 155                 160

Gly Asp Glu Thr Leu Asp Asp Asp Glu Trp Lys Leu Leu Tyr Glu Ala
                165                 170                 175

Ala Arg Asn Leu Ile Gly Val Ser Ser Thr Glu Phe Asp Gln Ser Ile
            180                 185                 190

Arg His Asn Thr Val Leu His Thr Leu Gln Lys Ala Phe Pro Asn Arg
        195                 200                 205

Gly Ile Lys Pro Leu Pro Leu Ala Cys His Arg Leu Ala Lys Gly Ser
    210                 215                 220

Pro Tyr Val Arg Trp His Ala Ala Asp Asn Val Tyr Tyr Asp Leu Phe
225                 230                 235                 240

Asp Gln Ser Leu Phe Gly Lys Val Asn Ser Glu Gly Ile Ala Arg Gly
                245                 250                 255

Lys Phe Phe Leu Leu Thr Asn Thr Arg Cys Thr Lys Leu His Thr Ser
            260                 265                 270

Asn Pro Asn Ala Thr Lys Asp Val Asn Val Gly Val Ala Glu Val Met
        275                 280                 285

Asp Leu Leu Ala Asp Arg Phe Thr Gly Ser Asp Gln His Lys Gln Val
    290                 295                 300

Ser Phe Ala Ile Asn Ala Lys Val Tyr Val Val Ala Ala Gly Ala Val
305                 310                 315                 320

Ala Thr Pro Gln Ile Leu Ala Asn Ser Asp Phe Gly Gly Leu Glu Gly
                325                 330                 335

Gln Gln Gly Lys Ala Leu Leu Pro Ala Leu Gly Val Gly Ile Thr Glu
            340                 345                 350

Gln Pro Leu Ala Phe Cys Gln Ile Ile Leu Asn Gln His Ile Val Asp
        355                 360                 365

Asp Leu Lys Asn Leu Asn Gly Arg Pro Gln Trp Trp Lys Asp Ala Val
    370                 375                 380

Glu Ala His Arg Arg Ala His Pro Lys Asp Pro Leu Trp Ile Pro Phe
385                 390                 395                 400

Gln Asp Pro Glu Pro Gln Val Asn Ile Pro Val Thr Lys Asp Phe Pro
                405                 410                 415

Trp His Ala Gln Ile His Arg Asp Ala Phe Ser Tyr Gly Glu Ala Gly
            420                 425                 430

Pro Arg Ala Asp Ser Arg Val Val Val Asp Leu Arg Phe Phe Ala Arg
        435                 440                 445

Gln Ala Arg Glu Pro Lys Asn Lys Leu Thr Phe Asp Lys Lys Ile Thr
    450                 455                 460

Asp Val Tyr Gly Met Pro Gln Pro Thr Phe Lys Tyr Leu Pro Thr Thr
465                 470                 475                 480

Gln Tyr Ala Asp Glu Ala Gly Lys Met Met Lys Asp Met Thr Glu Val
                485                 490                 495

Ala Ser Ala Leu Gly Gly Tyr Leu Pro Gly Ser Glu Pro Gln Phe Met
            500                 505                 510

Ala Pro Gly Leu Ala Leu His Leu Gly Gly Thr Val Arg Leu Gly His
        515                 520                 525

Gly Ser Glu Ile Asn Glu Ser Val Ala Asn Phe Asn Ser Gln Val Trp
    530                 535                 540

```
Asn Phe Lys Asn Leu Tyr Val Ala Gly Asn Gly Thr Ile Pro Thr Ala
545                 550                 555                 560

Phe Ala Ala Asn Pro Thr Leu Thr Ser Ile Ala Leu Ala Leu Arg Ala
                565                 570                 575

Thr His His Ile Val Lys Val Leu Lys Ala Asp Pro Asn Asn Leu Lys
            580                 585                 590

Pro Ala Val Pro Glu Glu Lys Leu Glu Ala Thr Pro Lys Glu Tyr Leu
        595                 600                 605

Lys Trp Leu Thr Asp Pro Thr Asn Pro Asp Phe Pro Asp His His Asp
    610                 615                 620

Leu Gln Lys Glu His Lys Glu Val Ile Val Lys Ala Glu Pro Ser His
625                 630                 635                 640

Thr Gly Gly Ser Gly Ser Gly His His His His His His
                645                 650


<210> SEQ ID NO 9
<211> LENGTH: 633
<212> TYPE: PRT
<213> ORGANISM: Phanerochaete chrysosporium

<400> SEQUENCE: 9

Met Phe Leu Asp Thr Thr Pro Phe Arg Ala Asp Glu Pro Tyr Asp Val
1               5                   10                  15

Phe Ile Ala Gly Ser Gly Pro Ile Gly Ala Thr Phe Ala Lys Leu Cys
            20                  25                  30

Val Asp Ala Asn Leu Arg Val Cys Met Val Glu Ile Gly Ala Ala Asp
        35                  40                  45

Ser Phe Thr Ser Lys Pro Met Lys Gly Asp Pro Asn Ala Pro Arg Ser
    50                  55                  60

Val Gln Phe Gly Pro Gly Gln Val Pro Ile Pro Gly Tyr His Lys Lys
65                  70                  75                  80

Asn Glu Ile Glu Tyr Gln Lys Asp Ile Asp Arg Phe Val Asn Val Ile
                85                  90                  95

Lys Gly Ala Leu Ser Thr Cys Ser Ile Pro Thr Ser Asn Asn His Ile
            100                 105                 110

Ala Thr Leu Asp Pro Ser Val Val Ser Asn Ser Leu Asp Lys Pro Phe
        115                 120                 125

Ile Ser Leu Gly Lys Asn Pro Ala Gln Asn Pro Phe Val Asn Leu Gly
    130                 135                 140

Ala Glu Ala Val Thr Arg Gly Val Gly Gly Met Ser Thr His Trp Thr
145                 150                 155                 160

Cys Ala Thr Pro Glu Phe Phe Ala Pro Ala Asp Phe Asn Ala Pro His
                165                 170                 175

Arg Glu Arg Pro Lys Leu Ser Thr Asp Ala Ala Glu Asp Ala Arg Ile
            180                 185                 190

Trp Lys Asp Leu Tyr Ala Gln Ala Lys Glu Ile Ile Gly Thr Ser Thr
        195                 200                 205

Thr Glu Phe Asp His Ser Ile Arg His Asn Leu Val Leu Arg Lys Tyr
    210                 215                 220

Asn Asp Ile Phe Gln Lys Glu Asn Val Ile Arg Glu Phe Ser Pro Leu
225                 230                 235                 240

Pro Leu Ala Cys His Arg Leu Thr Asp Pro Asp Tyr Val Glu Trp His
                245                 250                 255

Ala Thr Asp Arg Ile Leu Glu Glu Leu Phe Thr Asp Pro Val Lys Arg
            260                 265                 270
```

```
Gly Arg Phe Thr Leu Leu Thr Asn His Arg Cys Thr Lys Leu Val Phe
        275                 280                 285

Lys His Tyr Arg Pro Gly Glu Glu Asn Glu Val Asp Tyr Ala Leu Val
    290                 295                 300

Glu Asp Leu Leu Pro His Met Gln Asn Pro Gly Asn Pro Ala Ser Val
305                 310                 315                 320

Lys Lys Ile Tyr Ala Arg Ser Tyr Val Val Ala Cys Gly Ala Val Ala
                325                 330                 335

Thr Ala Gln Val Leu Ala Asn Ser His Ile Pro Pro Asp Asp Val Val
            340                 345                 350

Ile Pro Phe Pro Gly Gly Glu Lys Gly Ser Gly Gly Gly Glu Arg Asp
        355                 360                 365

Ala Thr Ile Pro Thr Pro Leu Met Pro Met Leu Gly Lys Tyr Ile Thr
    370                 375                 380

Glu Gln Pro Met Thr Phe Cys Gln Val Val Leu Asp Ser Ser Leu Met
385                 390                 395                 400

Glu Val Val Arg Asn Pro Pro Trp Pro Gly Leu Asp Trp Trp Lys Glu
                405                 410                 415

Lys Val Ala Arg His Val Glu Ala Phe Pro Asn Asp Pro Ile Pro Ile
            420                 425                 430

Pro Phe Arg Asp Pro Glu Pro Gln Val Thr Ile Lys Phe Thr Glu Glu
        435                 440                 445

His Pro Trp His Val Gln Ile His Arg Asp Ala Phe Ser Tyr Gly Ala
    450                 455                 460

Val Ala Glu Asn Met Asp Thr Arg Val Ile Val Asp Tyr Arg Phe Phe
465                 470                 475                 480

Gly Tyr Thr Glu Pro Gln Glu Ala Asn Glu Leu Val Phe Gln Gln His
                485                 490                 495

Tyr Arg Asp Ala Tyr Asp Met Pro Gln Pro Thr Phe Lys Phe Thr Met
            500                 505                 510

Ser Gln Asp Asp Arg Ala Arg Ala Arg Arg Met Met Asp Asp Met Cys
        515                 520                 525

Asn Ile Ala Leu Lys Ile Gly Gly Tyr Leu Pro Gly Ser Glu Pro Gln
    530                 535                 540

Phe Met Thr Pro Gly Leu Ala Leu His Leu Ala Gly Thr Thr Arg Cys
545                 550                 555                 560

Gly Leu Asp Thr Gln Lys Thr Val Gly Asn Thr His Cys Lys Val His
                565                 570                 575

Asn Phe Asn Asn Leu Tyr Val Gly Gly Asn Gly Val Ile Glu Thr Gly
            580                 585                 590

Phe Ala Ala Asn Pro Thr Leu Thr Ser Ile Cys Tyr Ala Ile Arg Ala
        595                 600                 605

Ser Asn Asp Ile Ile Ala Lys Phe Gly Arg His Arg Gly Gly Gly Ser
    610                 615                 620

Gly Ser Gly His His His His His His
625                 630
```

<210> SEQ ID NO 10
<211> LENGTH: 613
<212> TYPE: PRT
<213> ORGANISM: Aspergillus niger

<400> SEQUENCE: 10

```
Met Gln Tyr Ser Arg Met Thr Ala Thr Arg Glu Asn Pro Lys Tyr Lys
```

-continued

```
1               5                   10                  15

Asn Leu Arg Val Glu Glu Cys Asp Val Leu Ile Ile Gly Ser Gly Pro
            20                  25                  30

Val Gly Ala Thr Tyr Ala Arg Glu Ile Leu Asp Pro Gly Ser Gly Ala
        35                  40                  45

Ser Pro Gly Arg Lys Ala Pro Lys Val Ile Met Val Glu Thr Gly Ala
    50                  55                  60

Gln Glu Ser Lys Val Pro Gly Glu His Lys Lys Asn Ala Val Val Tyr
65                  70                  75                  80

Gln Lys His Ile Asp Ser Phe Val Asn Val Ile Gln Gly Ser Leu Phe
                85                  90                  95

Ala Thr Ser Val Pro Thr Arg Val Asp Pro Asn Leu Lys Leu Pro Pro
            100                 105                 110

Val Ser Trp Ser Pro Arg Glu Lys Gln Asn Phe Asn Gly Gln Asn Lys
        115                 120                 125

Glu Gln Asn Ile Tyr His Asn Leu Asp Ala Asn Gly Val Ser Arg Asn
    130                 135                 140

Val Gly Gly Met Ser Thr His Trp Thr Cys Ala Thr Pro Arg Gln His
145                 150                 155                 160

Glu Leu Glu Arg Ser Lys Ile Phe Asp Asp Ala Thr Trp Asp Arg Leu
                165                 170                 175

Tyr Lys Arg Ala Glu Glu Leu Ile Gly Thr Arg Thr Asp Val Leu Asp
            180                 185                 190

Gln Ser Ile Arg Gln Arg Leu Val Leu Asp Ile Leu Arg Lys Lys Phe
        195                 200                 205

Lys Asn Arg Asp Ala Lys Ala Leu Pro Leu Ala Ala Glu Lys Val Glu
    210                 215                 220

Gly Lys Asn Leu Ile Lys Trp Ser Ser Ser Ser Thr Val Leu Gly Asn
225                 230                 235                 240

Leu Leu Glu Asp Glu Lys Phe Thr Leu Leu Asp Gln His His Cys Glu
                245                 250                 255

Lys Leu Glu Phe Asn Asp Glu Thr Asn Lys Val Ser Phe Ala Ile Ile
            260                 265                 270

Lys Asn Leu Ala Lys Pro Gln Thr Ser Lys Glu Asp Glu Asp Arg Leu
        275                 280                 285

Arg Ile Lys Ala Lys Tyr Val Ile Val Cys Gly Gly Pro Ile Leu Thr
    290                 295                 300

Pro Gln Leu Leu Phe Lys Ser Gly Phe Arg Tyr Asp Glu Glu Asp Ala
305                 310                 315                 320

Glu Asp Ser Glu Gly Asn Lys Ser Ser Leu Tyr Ile Pro Ala Leu Gly
                325                 330                 335

Arg Asn Leu Thr Glu Gln Thr Met Cys Phe Cys Gln Ile Val Leu Lys
            340                 345                 350

Asp Lys Trp Val Glu Glu Leu Gln Lys Asn Asn Trp Gly Pro Glu Cys
        355                 360                 365

Glu Glu His Arg Arg Lys Tyr Asp Glu Glu Asp Asp Pro Leu Arg Ile
    370                 375                 380

Pro Phe Asp Asp Leu Asp Pro Gln Val Thr Leu Pro Phe Thr Glu Asn
385                 390                 395                 400

Thr Pro Trp His Thr Gln Ile His Arg Asp Ala Phe Ser Tyr Gly Ala
                405                 410                 415

Val Pro Pro Ala Ile Asp Lys Arg Thr Ile Val Asp Leu Arg Tyr Phe
            420                 425                 430
```

-continued

Gly Arg Ala Glu Thr Gln Trp Arg Asn Arg Val Thr Phe Ser Lys Lys
435 440 445

Leu Thr Asp Ala Tyr Gly Met Pro Gln Pro Thr Phe Asp Phe Lys Leu
450 455 460

Ser Thr Lys Asp Arg Leu Glu Ser His Arg Met Met Gln Asp Met Glu
465 470 475 480

Lys Val Ala Gly Glu Leu Gly Gly Tyr Leu Pro Gly Ser Glu Pro Gln
485 490 495

Phe Leu Ala Pro Gly Leu Ala Leu His Val Cys Gly Thr Thr Ala Ala
500 505 510

Leu Arg Lys Gly Cys Arg Ser Glu Asp Glu Met Lys Arg Ile Ser Val
515 520 525

Cys Asp Glu Asn Ser Lys Val Trp Gly Val Glu Asn Leu His Leu Gly
530 535 540

Gly Leu Asn Val Ile Pro Gly Pro Arg Ser Asn Ala Ser Asn Pro Thr
545 550 555 560

Leu Thr Ala Met Cys Phe Ala Ile Lys Gly Ala Glu Glu Ile Arg Arg
565 570 575

Lys Leu Gly Lys Lys Gly Ser His Ser Gly Asn Arg Asp Asp Gly Asp
580 585 590

Val Asp Thr Asp Thr Asp Asp Asp Ala Gly Gly Ser Gly Ser Gly His
595 600 605

His His His His His
610

<210> SEQ ID NO 11
<211> LENGTH: 635
<212> TYPE: PRT
<213> ORGANISM: Trametes multicolor

<400> SEQUENCE: 11

Met Ser Thr Ser Ser Ser Asp Pro Phe Phe Asn Phe Ala Lys Ser Ser
1 5 10 15

Phe Arg Ser Ala Ala Ala Gln Lys Ala Ser Ala Ser Ser Leu Pro Pro
20 25 30

Leu Pro Gly Pro Asp Lys Lys Val Pro Gly Met Asp Ile Lys Tyr Asp
35 40 45

Val Val Ile Val Gly Ser Gly Pro Ile Gly Cys Thr Tyr Ala Arg Glu
50 55 60

Leu Val Gly Ala Gly Tyr Lys Val Ala Met Phe Asp Ile Gly Glu Ile
65 70 75 80

Asp Ser Gly Leu Lys Ile Gly Ala His Lys Lys Asn Thr Val Glu Tyr
85 90 95

Gln Lys Asn Ile Asp Lys Phe Val Asn Val Ile Gln Gly Gln Leu Met
100 105 110

Ser Val Ser Val Pro Val Asn Thr Leu Val Val Asp Thr Leu Ser Pro
115 120 125

Thr Ser Trp Gln Ala Ser Thr Phe Phe Val Arg Asn Gly Ser Asn Pro
130 135 140

Glu Gln Asp Pro Leu Arg Asn Leu Ser Gly Gln Ala Val Thr Arg Val
145 150 155 160

Val Gly Gly Met Ser Thr His Trp Thr Cys Ala Thr Pro Arg Phe Asp
165 170 175

Arg Glu Gln Arg Pro Leu Leu Val Lys Asp Asp Ala Asp Ala Asp Asp

-continued

```
            180                 185                 190

Ala Glu Trp Asp Arg Leu Tyr Thr Lys Ala Glu Ser Tyr Phe Gln Thr
        195                 200                 205

Gly Thr Asp Gln Phe Lys Glu Ser Ile Arg His Asn Leu Val Leu Asn
    210                 215                 220

Lys Leu Thr Glu Glu Tyr Lys Gly Gln Arg Asp Phe Gln Gln Ile Pro
225                 230                 235                 240

Leu Ala Ala Thr Arg Arg Ser Pro Thr Phe Val Glu Trp Ser Ser Ala
                245                 250                 255

Asn Thr Val Phe Asp Leu Gln Asn Arg Pro Asn Thr Asp Ala Pro Glu
            260                 265                 270

Glu Arg Phe Asn Leu Phe Pro Ala Val Ala Cys Glu Arg Val Val Arg
        275                 280                 285

Asn Ala Leu Asn Ser Glu Ile Glu Ser Leu His Ile His Asp Leu Ile
    290                 295                 300

Ser Gly Asp Arg Phe Glu Ile Lys Ala Asp Val Tyr Val Leu Thr Ala
305                 310                 315                 320

Gly Ala Val His Asn Thr Gln Leu Leu Val Asn Ser Gly Phe Gly Gln
                325                 330                 335

Leu Gly Arg Pro Asn Pro Ala Asn Pro Pro Glu Leu Leu Pro Ser Leu
            340                 345                 350

Gly Ser Tyr Ile Thr Glu Gln Ser Leu Val Phe Cys Gln Thr Val Met
        355                 360                 365

Ser Thr Glu Leu Ile Asp Ser Val Lys Ser Asp Met Thr Ile Arg Gly
    370                 375                 380

Thr Pro Gly Glu Leu Thr Tyr Ser Val Thr Tyr Thr Pro Gly Ala Ser
385                 390                 395                 400

Thr Asn Lys His Pro Asp Trp Trp Asn Glu Lys Val Lys Asn His Met
                405                 410                 415

Met Gln His Gln Glu Asp Pro Leu Pro Ile Pro Phe Glu Asp Pro Glu
            420                 425                 430

Pro Gln Val Thr Thr Leu Phe Gln Pro Ser His Pro Trp His Thr Gln
        435                 440                 445

Ile His Arg Asp Ala Phe Ser Tyr Gly Ala Val Gln Gln Ser Ile Asp
    450                 455                 460

Ser Arg Leu Ile Val Asp Trp Arg Phe Phe Gly Arg Thr Glu Pro Lys
465                 470                 475                 480

Glu Glu Asn Lys Leu Trp Phe Ser Asp Lys Ile Thr Asp Ala Tyr Asn
                485                 490                 495

Met Pro Gln Pro Thr Phe Asp Phe Arg Phe Pro Ala Gly Arg Thr Ser
            500                 505                 510

Lys Glu Ala Glu Asp Met Met Thr Asp Met Cys Val Met Ser Ala Lys
        515                 520                 525

Ile Gly Gly Phe Leu Pro Gly Ser Leu Pro Gln Phe Met Glu Pro Gly
    530                 535                 540

Leu Val Leu His Leu Gly Gly Thr His Arg Met Gly Phe Asp Glu Lys
545                 550                 555                 560

Glu Asp Asn Cys Cys Val Asn Thr Asp Ser Arg Val Phe Gly Phe Lys
                565                 570                 575

Asn Leu Phe Leu Gly Gly Cys Gly Asn Ile Pro Thr Ala Tyr Gly Ala
            580                 585                 590

Asn Pro Thr Leu Thr Ala Met Ser Leu Ala Ile Lys Ser Cys Glu Tyr
        595                 600                 605
```

-continued

```
Ile Lys Gln Asn Phe Thr Pro Ser Pro Phe Thr Ser Glu Ala Gln Gly
    610                 615                 620

Gly Ser Gly Ser Gly His His His His His His
625                 630                 635
```